US012763190B2

(12) United States Patent
Kiani et al.

(10) Patent No.: US 12,763,190 B2
(45) Date of Patent: Oct. 13, 2026

(54) SYSTEMS AND METHODS FOR AN OPTIMIZED USER INTERFACE

(71) Applicant: Willow Laboratories, Inc., Irvine, CA (US)

(72) Inventors: Massi Joe E. Kiani, Laguna Niguel, CA (US); Don Sanders, Irvine, CA (US)

(73) Assignee: Willow Laboratories, Inc., Irvine, CA (US)

( * ) Notice: Subject to any disclaimer, the term of this patent is extended or adjusted under 35 U.S.C. 154(b) by 169 days.

(21) Appl. No.: 18/782,451

(22) Filed: Jul. 24, 2024

(65) Prior Publication Data

US 2025/0037836 A1 Jan. 30, 2025

Related U.S. Application Data

(60) Provisional application No. 63/515,454, filed on Jul. 25, 2023.

(51) Int. Cl.
*G16H 20/60* (2018.01)
*G06F 9/451* (2018.01)

(52) U.S. Cl.
CPC ............. *G16H 20/60* (2018.01); *G06F 9/451* (2018.02)

(58) Field of Classification Search
CPC ................................ G16H 20/60; G06F 9/451
See application file for complete search history.

(56) References Cited

U.S. PATENT DOCUMENTS

| | | | | |
|---|---|---|---|---|
| 12,437,192 | B1 * | 10/2025 | Neagu | G06F 9/542 |
| 2010/0153781 | A1 * | 6/2010 | Hanna | G06F 21/577 714/E11.178 |
| 2012/0210251 | A1 * | 8/2012 | Abrams | G06F 3/0482 715/753 |
| 2015/0223705 | A1 * | 8/2015 | Sadhu | A61B 5/0006 600/595 |
| 2020/0077942 | A1 * | 3/2020 | Youngblood | A61B 5/4812 |
| 2021/0118545 | A1 * | 4/2021 | Sathyanarayana | G06N 5/04 |
| 2021/0255945 | A1 * | 8/2021 | Ikeuchi | G06F 11/34 |
| 2022/0176065 | A1 * | 6/2022 | Youngblood | G06F 3/011 |

* cited by examiner

*Primary Examiner* — Tadesse Hailu
(74) *Attorney, Agent, or Firm* — KNOBBE, MARTENS, OLSON & BEAR, LLP

(57) ABSTRACT

A computing system may include non-transitory computer-readable media storing instructions that when executed by the one or more computer processors, causes the computing system to perform operations comprising: causing presentation of a graphical user interface, the graphical user interface being associated with patient health data, wherein the graphical user interface is configured to: display one or more user interface elements, receive information identifying a logging action and at least one classification associated with the logging action, generate, by the processor, one or more models based on the received information, based on the generated one or more models, automatically associate the one or more user interface elements with one or more logging actions and update the graphical user interface with at least a portion of the one or more user interface elements.

20 Claims, 24 Drawing Sheets

800A

| Item to log 802A | Weekly Frequency (Estimate) 804A |
|---|---|
| Water | 3 |
| Coffee | 2 |
| Brand 1 Vege Mac & Cheese | 2 |
| Brand 1 Vegan Mac & Cheese | 1 |
| Beverage 1 | 1 |
| Restaurant 1 Cheese Pizza | 0.5 |
| Restaurant 1 Cheese Pizza ½ Pineapple | 0.5 |
| Restaurant 1 Cheesy Bread | 0.5 |
| Restaurant 1 Garden Salad | 0.25 |
| Restaurant 1 Garlic Dip | 0.1 |
| | 10.85 = F |

806A

FIG. 8A

| Symbol | A | B | C | D | E |
|---|---|---|---|---|---|
| Probabilities | 0.385 | 0.179 | 0.154 | 0.154 | 0.128 |
| First Division | 0 | | 1 | | |
| Second Division | 0 | 1 | 0 | 1 | |
| Third Division | | | | 0 | 1 |
| Codewords | 00 | 01 | 10 | 110 | 111 |

800F

1002A

Decision Tree Examples

| | Example |
|---|---|
| Variable | Meal Location |
| Condition | Meal Location == Home |
| Rule Set | (Meal Location == Home, Meal Prev == Healthy, Meal Time == Noon, Meal Day == Saturday) |
| Habit/Pattern | (Meal Location == Home, Meal Prev == Healthy, Meal Time == Noon, Meal Day == Saturday) => Healthy Meal |

| User Id = 0001, Date = 12/05/2020 (Saturday) | |
|---|---|
| 8:00AM | Wake Up, Sad |
| 8:30AM | Omelet (1 Large), Low Hunger, Home, Sad |
| 12:30PM | Salad (1 Serving), Mid Hunger, Home, Sad |
| 1:00PM | Walk (2hrs), Tired |
| 6:30PM | Steak (8 Once), Sweet Tea (1 Serving), High Hunger, Home, Sad |
| 11:30PM | Sleep, Relaxed |

Pre-Processing

| User Id | Time of Day | Day of Week | Hunger | Emotion | Loc | Activity | label |
|---|---|---|---|---|---|---|---|
| 0001 | Noon | Weekend | Mid | Sad | Home | Low Level | Healthy |
| 0001 | Evening | Weekend | High | Sad | Home | Low Level | Unhealthy |

Feature Extraction

| User Id | Time of Day | Day of Week | Hunger | Emotion | Loc | Activity | Label | Label Next Meal |
|---|---|---|---|---|---|---|---|---|
| 0001 | Noon | Weekend | Mid | Sad | Home | Low Level | Healthy | Unhealthy |

FIG. 10B

Clustering Examples

1004A $$F_{i,j} = \frac{\text{Count (pattern } i\text{,user } j)}{\sum \text{Count (pattern } k\text{,user } j)}$$

| | User 1 | User 2 | ••• | User m |
|---|---|---|---|---|
| Pattern 1 | $f_{1,1}$ | $f_{1,2}$ | ••• | $f_{1,m}$ |
| Pattern 2 | $f_{2,1}$ | $f_{2,2}$ | ••• | $f_{2,m}$ |
| ••• | ••• | ••• | ••• | ••• |
| Pattern n | $f_{n,1}$ | $f_{n,2}$ | ••• | $f_{n,m}$ |

FIG. 10D

1008A

Correlation-Based Nudge

| | Population | Duration | Variable | Missing Data |
|---|---|---|---|---|
| **Training** | NA | NA | NA | NA |
| **Prediction** | Target User Data | 14 Days Rolling Window | Food, Activity, Sleep | • Missing Data Treated as Category "Missing". • No Nudge is Given if No Correlation Detected. |

FIG. 10F

1010A

Dependency Analysis

$$X^2 = \sum \frac{(O_i - E_i)^2}{E_i}$$

| | Population | Duration | Variable | Missing Data |
|---|---|---|---|---|
| **Training** | NA | NA | NA | NA |
| **Prediction** | Target User Data | • Power> .8 (Chi-Square Value and DOF) • Rule of Thumb: 60-500 | Food, Activity, Sleep | • Missing Data Treated as Category "Missing". • No Nudge is Given if No Dependency Detected. |

FIG. 10G

1012A

Temporal Event Model

| | Population | Duration | Variable | Missing Data |
|---|---|---|---|---|
| **Training** | NA | NA | NA | NA |
| **Prediction** | Target User Data | 75 Days | Food, Activity, Sleep | 5%-10% Missing Data tolerance |

FIG. 10H

1012B

Temporal Event Model

| User Id = 0001, Date = 12/05/2020 (Saturday) | |
|---|---|
| 8:00AM | Wake Up, Sad |
| 8:30AM | Omelet (1 Large), Low Hunger, Home, Sad |
| 12:30PM | Salad (1 Serving), Mid Hunger, Home, Sad |
| 1:00PM | Bike (2hrs), Tired |
| 6:30PM | Steak (8 Once), Sweet Tea (1 Serving), High Hunger, Home, Sad |
| 11:30PM | Sleep, Relaxed |

| Time | Event |
|---|---|
| 8:00AM | Wake Up |
| 8:30AM | Breakfast |
| 12:30PM | Lunch |
| 1:00PM | Walk |
| 6:30PM | Dinner |
| 11:30PM | Weekend Sleep |

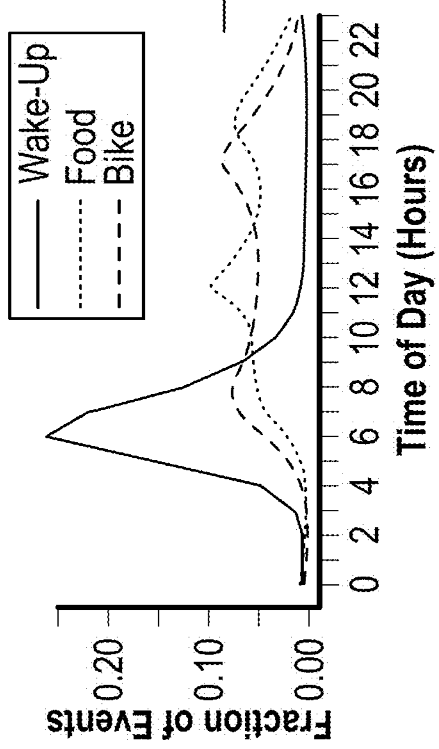

$$\lambda_u(t,a) = \alpha_{ua} + Time_u(t,a)$$

Event Intensity Personalization Propensity $$Time_u(t,a) = \sum_{z \in Z} \frac{\beta_{az}}{\sqrt{2\pi\sigma_{az}^2}} exp\left(-\frac{(l_t-\mu_{az})^2}{2\sigma_{az}^2}\right)$$

FIG. 10I

1012C

Temporal Event Model

Advanced Model for Long Term

Simplified Model for Short Term $$\lambda_u(t, a) = \alpha_{ua} + Time_u(t, a) + ShortTerm_u(t, a) + LongTerm_u(t, a)$$

Event Intensity Personallization Propensity Short-Term Dependency Long-Term Dependency

| Dataset | No. of Events | Population | Duration | No. of Samples |
|---|---|---|---|---|
| Argus (Azumio) | 10 (Drink, Sleep, Heart Rate, Running, Weight, Food, Walking, Biking, Workout and Stretching) | 4,000 | 7 Month | 2.1 Million |
| MyFitnessPal (UA) | 8 (Running, Walking, Biking, Workout, Breakfast, Lunch, Dinner, and Snacks) | 15,000 | 10 Month | 9.8 Million |

FIG. 10J

SYSTEMS AND METHODS FOR AN OPTIMIZED USER INTERFACE

CROSS REFERENCE TO RELATED APPLICATIONS

The present application claims priority to U.S. Provisional Patent Application No. 63/515,454, entitled "SYSTEMS AND METHODS FOR AN OPTIMIZED USER INTERFACE," filed on Jul. 25, 2023, the contents of which are incorporated by reference herein.

FIELD OF THE DISCLOSURE

The present disclosure relates to systems and methods for optimizing a user interface for a health system.

BACKGROUND OF THE INVENTION

A background is provided for introductory purposes and to aid the reader in understanding the detailed description. The background should not be taken as an admission of any prior art to the claims.

Individuals at risk of certain lifestyle diseases, such as diabetes, cardiovascular disease, and stroke can conventionally receive health and wellness care through a variety of behavioral, clinical, or social programs, such as calorie counting applications, fitness trackers, weight loss support groups, and clinical care. However, many people have difficulty complying with these programs and ultimately fail to improve their health. Computers can be programmed to perform calculations and operations utilizing computer-based habit modeling. Various techniques have been developed to minimize the effort required by a human user in in adapting and reprogramming the computer for utilizing such computer-based habit models.

SUMMARY OF THE INVENTION

The systems and methods, and devices described herein each have several aspects, no single one of which is solely responsible for its desirable attributes. Without limiting the scope of this disclosure, several non-limiting features will now be described briefly.

The health of a person can hinge on a variety of behavioral, genetic, social, and other factors. In particular, behavioral and social factors such as diet, exercise, sleep, and stress are significant contributors to the development of so-called lifestyle diseases, such as heart disease, stroke, and type 2 diabetes. To persons at risk for developing such diseases, the general notion of reducing their risk through a regimen of stress reduction, sleeping more, eating better and exercising regularly may be known and understood. However, compliance with such a regimen is difficult. While there are programs that may aid a person with following such a regimen, they typically only address a limited number of factors that contribute to a person's health, such as merely diet and exercise. Such a segmented approach is of limited help to a person trying to change their lifestyle because it ignores other important factors that may significantly contribute to the person's health risk. Furthermore, lifestyle programs rarely take into account the fuller picture of a person's health beyond merely weight gain or loss in monitoring progress.

Doctors and healthcare professionals alike encourage their patients to participate in lifestyle programs. A patient is more likely to keep up with a lifestyle program if the program is user-friendly, meaning the program is designed with the specific patient's preferences in mind. One aspect often overlooked in a lifestyle program's design is the efficiency of the GUI presented to the patient, and the patient's interaction with the GUI. An inefficient GUI can result in unnecessary interactions with the GUI, such as additional clicks or touches on a screen to log a health-related event. A patient can become frustrated by an interaction with a lifestyle program that inefficiently presents information, feeling as if the lifestyle program is wasting valuable time. A designer may attempt to alleviate these frustrations by generating user-centered designs, creating a clear and consistent layout, or defining an intuitive navigation of pages. However, a designer's attempts to generate an efficient GUI may fall short as individual subscribers can have varying habits that must be accounted for. Patients using an inefficient GUI may be less likely to stay in a lifestyle program, thus diminishing their overall health goals.

Disclosed herein is a health system and methods that aims to help its users make better meal and lifestyle choices by providing a user with an easily accessible and efficient GUI. The efficient GUI can reduce the number of clicks required to log an event into, for example, a health management system. The system achieves this goal, in part, by generating one or more models based the frequency an event is logged. The generated models may be used in conjunction with an ontology, such as a classification hierarchy, to update a GUI. The updated GUI can provide a user with the most efficient selection of logging events based on the user's previous selections.

In some aspects, the techniques described herein relate to a computing system including: one or more processors; and non-transitory computer-readable media storing instructions that when executed by the one or more computer processors, causes the computing system to perform operations including: causing presentation of a graphical user interface, the graphical user interface being associated with patient health data, wherein the graphical user interface is configured to: display one or more user interface elements, wherein each user interface element is associated with one or more logging actions and one or more classifications; receive information identifying a logging action and at least one classification associated with the logging action; generate by the processor, one or more models based on the received information, wherein at least one model includes: a probability distribution of the one or more logging actions for a combination of the one or more classifications, wherein the probability distribution is created by assigning a probability to each of the one or more logging actions based on a weighted sum of a likelihood that a user will select at least one logging action from the one or more logging actions; based on the generated one or more models, automatically associate the one or more user interface elements with one or more logging actions based on the assigned probability of each logging action; and update the graphical user interface with at least a portion of the one or more user interface elements, wherein the updated graphical user interface displays one or more logging actions based on the likelihood that a user will select the logging action.

In some aspects, the techniques described herein relate to a computing system, wherein the one or more logging actions includes at least one of: an item of consumption or a physical activity.

In some aspects, the techniques described herein relate to a computing system, wherein the at least one classification includes at least one of a user ID, a time of day, a day of week, a location, an activity level, a hunger level, an emotion, or a label.

In some aspects, the techniques described herein relate to a computing system, wherein a time of day includes at least one of Morning (5 AM-11 AM); Midday (11 AM-5 PM); or Evening (5 PM-11 PM).

In some aspects, the techniques described herein relate to a computing system, wherein the location includes at least one of a latitude and longitude, a home, a gym, or an office.

In some aspects, the techniques described herein relate to a computing system, wherein the activity level is at least one of low-level, mid-level, or high-level.

In some aspects, the techniques described herein relate to a computing system, wherein the hunger level is at least one of low, mid, or high.

In some aspects, the techniques described herein relate to a computing system, wherein the emotion is at least one of happy, relaxed, sad, bored, stressed, angry, worried, fearful, guilty, or prideful.

In some aspects, the techniques described herein relate to a computing system, wherein the label is at least one of healthy and unhealthy, and wherein healthy is associated with at least one logging action that is less than 500 calories, and wherein unhealthy includes a logging action that is 500 calories or more.

In some aspects, the techniques described herein relate to a computing system, wherein the graphical user interface is further configured to: validate the one or more models for accuracy, by the processor, prior to automatically associating the one or more user interface elements with the one or more logging actions, and wherein validating the one or more models includes: comparing the weighted sum of the logging actions for the one or more generated models to a threshold weighted sum.

In some aspects, the techniques described herein relate to a computing system, wherein the graphical user interface is further configured to: in response to a validated model, by the processor, adjust an efficiency improvement threshold for one or more portions of the graphical user interface.

In some aspects, the techniques described herein relate to a computing system, wherein the graphical user interface is further configured to: in response to a validated model, associate a second user interface element with an indication that the one or more models are valid; and automatically update the graphical user interface to display the second user interface element.

In some aspects, the techniques described herein relate to a computing system, wherein the one or more models include one or more constraints, and wherein the one or more constraints include at least one of a filter to exclude changes that yield marginal improvement but require substantial user interface changes, a rule defining how one or more inputs to the model can be combined, or a large language model used for predicting a next word of logging action or a classification based on a user input.

In some aspects, the techniques described herein relate to a computing system, wherein the graphical user interface is further configured to: prior to associating the one or more user interface elements with the one or more logging actions based on the assigned probability of each logging action, associate a second user interface element with a request for a user input; and automatically updating the graphical user interface to display the second user interface element.

In some aspects, the techniques described herein relate to a computing system, wherein the graphical user interface is further configured to: receive information identifying a request to associate the one or more user interface elements with the one or more logging actions based on the assigned probability of each logging action.

In some aspects, the techniques described herein relate to a computing system as described herein.

In some aspects, the techniques described herein relate to a computer-implemented method of generating an efficient graphical user interface including: by a system of one or more processors: displaying one or more user interface elements, wherein each user interface element is associated with one or more logging actions and one or more classifications; receiving information identifying a logging action and at least one classification associated with the logging action; generating by the processor, one or more models based on the received information, wherein at least one model includes: a probability distribution of the one or more logging actions for a combination of the one or more classifications, wherein the probability distribution is created by assigning a probability to each of the one or more logging actions based on a weighted sum of a likelihood that a user will select at least one logging action from the one or more logging actions; based on the generated one or more models, automatically associating the one or more user interface elements with one or more logging actions based on the assigned probability of each logging action; and updating the graphical user interface with at least a portion of the one or more user interface elements, wherein the updated graphical user interface displays one or more logging actions based on the likelihood that a user will select the logging action.

In some aspects, the techniques described herein relate to a computer-implemented method, wherein the one or more logging actions includes at least one of an item of consumption or a physical activity.

In some aspects, the techniques described herein relate to a computer-implemented method, wherein the at least one classification includes at least one of a user ID, a time of day, a day of week, a location, an activity level, a hunger level, an emotion, or a label.

In some aspects, the techniques described herein relate to a computer-implemented method, wherein a time of day includes at least one of Morning (5 AM-11 AM); Midday (11 AM-5 PM); or Evening (5 PM-11 PM).

In some aspects, the techniques described herein relate to a computer-implemented method, wherein the location includes at least one of a latitude and longitude, a home, a gym, or an office.

In some aspects, the techniques described herein relate to a computer-implemented method, wherein the activity level is at least one of low-level, mid-level, or high-level.

In some aspects, the techniques described herein relate to a computer-implemented method, wherein the hunger level is at least one of low, mid, or high.

In some aspects, the techniques described herein relate to a computer-implemented method, wherein the emotion is at least one of happy, relaxed, sad, bored, stressed, angry, worried, fearful, guilty, or prideful.

In some aspects, the techniques described herein relate to a computer-implemented method, wherein the label is at least one of healthy and unhealthy, and wherein healthy is associated with at least one logging action that is less than 500 calories, and wherein unhealthy is associated with at least one logging action that is 500 calories or more.

In some aspects, the techniques described herein relate to a computer-implemented method, wherein the method further includes: validating the one or more models for accuracy, by the processor, prior to automatically associating the one or more user interface elements with one or more logging actions, and wherein validating the one or more models includes: comparing the weighted sum of the logging actions for the one or more generated models to a threshold weighted sum.

In some aspects, the techniques described herein relate to a computer-implemented method, wherein the method further includes: in response to a validated model, by the processor, adjusting an efficiency improvement threshold for one or more portions of the graphical user interface.

In some aspects, the techniques described herein relate to a computer-implemented method, wherein the method further includes: in response to a validated model, associating a second user interface element with an indication that the one or more models are valid; and automatically updating the graphical user interface to display the second interface element.

In some aspects, the techniques described herein relate to a computer-implemented method, wherein the one or more models include one or more constraints, and wherein the one or more constraints include at least one of a filter to exclude changes that yield marginal improvement but require substantial user interface changes, a rule defining how one or more inputs to the model can be combined, or a large language model used for predicting a next word of a logging action or a classification based on a user input.

In some aspects, the techniques described herein relate to a computer-implemented method, wherein the method further includes: prior to associating the one or more user interface elements with the one or more logging actions based on the assigned probability of each logging action, associating a second user interface element with a request for a user input; and automatically updating the graphical user interface to display the second user interface element.

In some aspects, the techniques described herein relate to a computer-implemented method, wherein the method further includes: receiving information identifying a request to associate the one or more user interface elements with the one or more logging actions based on the assigned probability of each logging action.

In some aspects, the techniques described herein relate to a computer-implemented method as described herein. According to various implementations, large amounts of data are automatically and dynamically calculated interactively in response to user inputs, and the calculated data is efficiently and compactly presented to a user by the system. Thus, in some implementations, the user interfaces described herein are more efficient as compared to previous user interfaces in which data is not dynamically updated and compactly and efficiently presented to the user in response to interactive inputs.

Further, as described herein, the system may be configured and/or designed to generate user interface data useable for rendering the various interactive user interfaces described. The user interface data may be used by the system, and/or another computer system, device, and/or software program (for example, a browser program), to render the interactive user interfaces. The interactive user interfaces may be displayed on, for example, electronic displays (including, for example, touch-enabled displays).

Additionally, it has been noted that design of computer user interfaces that are useable and easily learned by humans is a non-trivial problem for software developers. The present disclosure describes various implementations of interactive and dynamic user interfaces that are the result of significant development. This non-trivial development has resulted in the user interfaces described herein which may provide significant cognitive and ergonomic efficiencies and advantages over previous systems. The interactive and dynamic user interfaces include improved human-computer interactions that may provide reduced mental workloads, improved decision-making, reduced work stress, and/or the like, for a user. For example, user interaction with the interactive user interface via the inputs described herein may provide an optimized display of, and interaction with, models and model-related data, and may enable a user to more quickly and accurately access, navigate, assess, and digest the model-related data than previous systems.

Further, the interactive and dynamic user interfaces described herein are enabled by innovations in efficient interactions between the user interfaces and underlying systems and components. For example, disclosed herein are improved methods of receiving user inputs (including methods of interacting with, managing, and minimizing the average number of presses for a user to log an action), translation and delivery of those inputs to various system components, automatic and dynamic execution of complex processes in response to the input delivery, automatic interaction among various components and processes of the system, and automatic and dynamic updating of the user interfaces (to, for example, display the health-related data). The interactions and presentation of data via the interactive user interfaces described herein may accordingly provide cognitive and ergonomic efficiencies, among various additional technical advantages over previous systems.

Thus, various implementations of the present disclosure can provide improvements to various technologies and technological fields, and practical applications of various technological features and advancements. For example, as described above, existing computer-based modeling technology is limited in various ways, and various implementations of the disclosure provide significant technical improvements over such technology. Additionally, various implementations of the present disclosure are inextricably tied to computer technology. In particular, various implementations rely on operation of technical computer systems and electronic data stores, automatic processing of electronic data, and the like. Such features and others (e.g., processing and analysis of large amounts of electronic data, management of data migrations and integrations, and/or the like) are intimately tied to, and enabled by, computer technology, and would not exist except for computer technology. For example, the interactions with, and management of, computer-based health data described below in reference to various implementations cannot reasonably be performed by humans alone, without the computer technology upon which they are implemented. Further, the implementation of the various implementations of the present disclosure via computer technology enables many of the advantages described herein, including more efficient management of various types of electronic data (including computer-based health data).

Various combinations of the above and below recited features, embodiments, implementations, and aspects are also disclosed and contemplated by the present disclosure.

Additional implementations of the disclosure are described below in reference to the appended claims, which may serve as an additional summary of the disclosure.

In various implementations, systems and/or computer systems are disclosed that comprise a computer-readable storage medium having program instructions embodied therewith, and one or more processors configured to execute the program instructions to cause the systems and/or computer systems to perform operations comprising one or more aspects of the above- and/or below-described implementations (including one or more aspects of the appended claims).

In various implementations, computer-implemented methods are disclosed in which, by one or more processors executing program instructions, one or more aspects of the above- and/or below-described implementations (including one or more aspects of the appended claims) are implemented and/or performed.

In various implementations, computer program products comprising a computer-readable storage medium are disclosed, wherein the computer-readable storage medium has program instructions embodied therewith, the program instructions executable by one or more processors to cause the one or more processors to perform operations comprising one or more aspects of the above- and/or below-described implementations (including one or more aspects of the appended claims).

BRIEF DESCRIPTION OF THE DRAWINGS

FIG. 8A-8F illustrates example implementations for optimizing a GUI to efficiently log one or more actions.

FIGS. 10A-10J depict an example implementation of a habit modeling framework.

DETAILED DESCRIPTION OF THE PREFERRED EMBODIMENT

Figure 1:
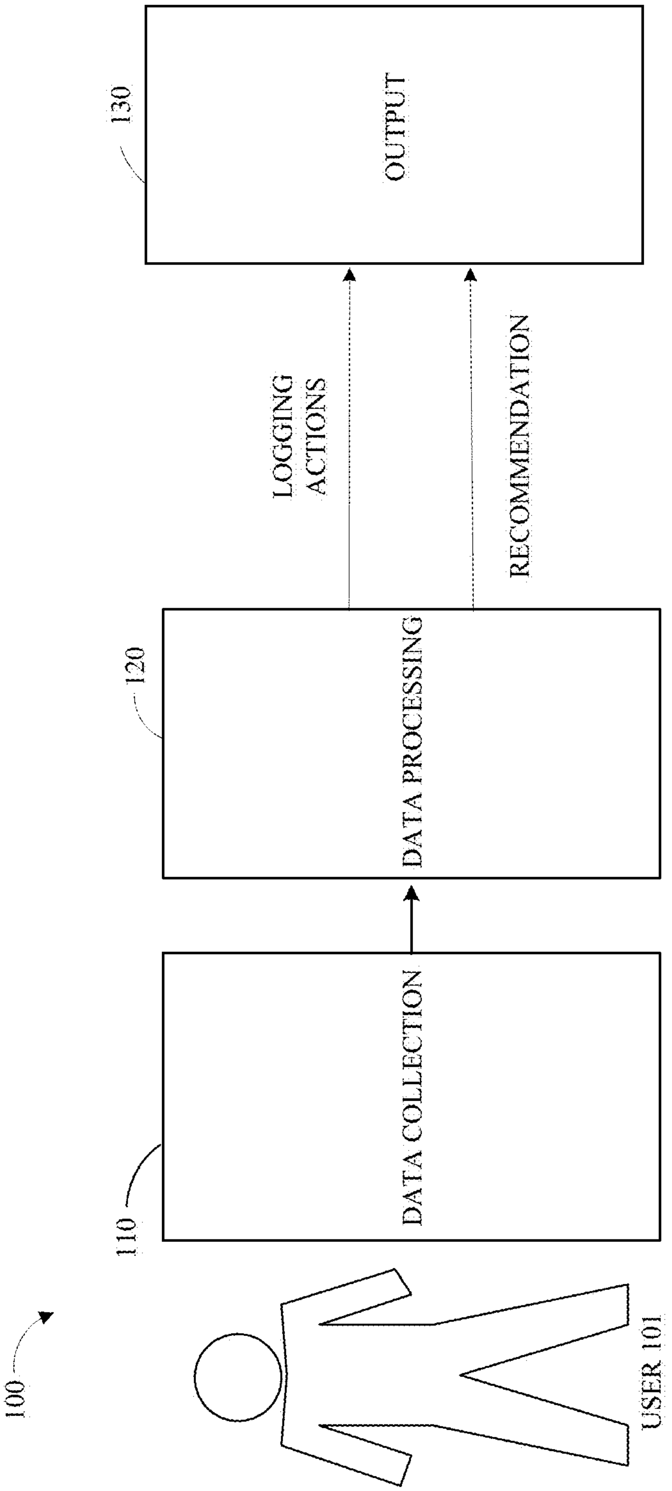
FIG. 1 shows a block diagram of an example health system.

Although certain preferred implementations, embodiments, and examples are disclosed below, the inventive subject matter extends beyond the specifically disclosed implementations to other alternative implementations and/or uses and to modifications and equivalents thereof. Thus, the scope of the claims appended hereto is not limited by any of the particular implementations described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain implementations; however, the order of description should not be construed to imply that these operations are order dependent. Additionally, the structures, systems, and/or devices described herein may be embodied as integrated components or as separate components. For purposes of comparing various implementations, certain aspects and advantages of these implementations are described. Not necessarily all such aspects or advantages are achieved by any particular implementation. Thus, for example, various implementations may be carried out in a manner that achieves or optimizes one advantage or group of advantages as taught herein without necessarily achieving other aspects or advantages as may also be taught or suggested herein.

Overview

A health system may request that a user log one or more actions based on the user's lifestyle choices. Determining and presenting an optimized GUI to a user may include systems and methods for not only collecting comprehensive data regarding behavioral, physiological, and other health related data associated with a user, but also effectively analyzing the collected data to organize and present the user with a personalized list of selection-based habits and patterns of the user. Advantageously, the GUI may effectively reduce the average number of presses for a user to log an action. The health system may provide coaching recommendations, insights, encouragements, or the like. The health system described herein may include various systems and methods for determining and presenting an efficient GUI to a user of the system by collecting and processing data based on user inputs and habits, and updating a GUI based on a predicted next logging action. The health system disclosed herein may help users make better meal and lifestyle choices, remain in health improvement programs by providing an easy-to-use and efficient GUI, and reduce or eliminate frustration when attempting to log a health-related action. The health system may achieve these goals by using various interactive tools and processes, such as training an AI model to predict a next logging action, leveraging entropy encoding, referencing one or more databases such as a hypernym database and/or a database based on another ontology, conducting an onboarding process, and/or habit modeling.

FIG. 1 shows a block diagram of an example health system 100 (referred to hereinafter as "system 100"). The system 100 may include, but is not limited to, a data collection block 110 to collect or access data related to a user 101, a data processing block 120 for analyzing user data from data collection block 110 to determine information related to a user health, and an output 130.

At a data collection block 110, the system 100 can include one or more processes for collecting any number of different types of data from any number of sources. For example, a system 100 may receive sensor data associated with one or more physiological parameters from at least one physiological sensor, such as a glucose sensor or monitor, smart watch, mobile device, photoplethysmographic sensor, EEG sensor, ECG sensor, the like or a combination thereof. In some examples, a system 100 can include data collected from non-sensor based sources, including but not limited to user input, third party input, device tracking data, or the like. Advantageously, the system 100 can provide more inclusive, comprehensive, and effective coaching over systems with device specific data collection by collecting data from a number of different data sources. For example, as described below with reference to FIG. 5, the data can include device tracking data, third party data, user input data, or other user related data. Additionally and/or alternatively, the data collection block 110 can be used to update a database of logging actions and classifications.

A logging action can include any type of health-related information that a user of a system 100 desires to log, such as a consumable item, a physical activity, and/or the like. One or more logging actions may be displayed on a GUI for selection by a user 101. For example, the logging action can be related to exercise (such as a type of exercise including but not limited to yoga, jogging, swimming, weight-lifting, stretching and/or the like), a consumable item (such as but not limited to a water, coffee, fruit, vegetables, potato chips, pizza, burrito, cheeseburger, salad and/or the like), medications, vitamin supplements, shots or injections or the like. Each logging action can be associated with one or more classifications.

Classifications can be any data describing or defining one or more characteristics of a logging action, and/or another classification. associated with the logging action. In some implementations, a classification can be automatically associated with a logging action. In some implementations, a user may select one or more classifications for a selected logging action. In one example, a logging action can be associated with one or more classifications, including a user ID for the associated logging action, a time of day, a day of week, a location, an activity level, a hunger level, an emotion, or any other label that may be associated with a logging action. In some implementations, a classification can include a time of day of at least one of Morning (5 AM-11 AM); Midday (11 AM-5 PM); or Evening (5 PM-11 PM). In one implementation, a classification can be a location including at least a latitude and/or longitude, a home, a gym, an office and/or the like. In one implementation, classification can be an activity level that is at least one of a low-level, a medium-level, a high-level and/or the like. In one implementation, a classification can be an emotion including but not limited to happy, relaxed, sad, bored, stressed, angry, worried, fearful, guilty, prideful and/or the like. In one implementation a classification of a logging action can include a label. An example of a label can include either healthy and/or unhealthy. The system 100 can determine which label to apply based on additional information about the logging action. For example, a label of "unhealthy" may be placed on logging actions having a total calorie count above 500 calories, which a label of "healthy" may be placed on logging actions having a total calorie count at 500 or less calories.

At a data processing block 120, the system 100 can process the user data from block 110 and transmit the updated data to a user device to produce an efficient GUI to reduce the number of presses required to select a logging action. Additionally and/or alternatively, data processing block 120 can process health risk information, health recommendation information, or another output associated with the user, the system 100, a user's health condition, a user device, and the like or a combination thereof. Advantageously, the data processing block 120 may use a variety of user data to generate one or more outputs. For example, the data processing block 120 may determine a relationship between logging actions, classifications, physiological factors, such as blood glucose and heart rate, and behavioral factors, such as sleep, dietary data, and activity information, to generate a uniquely personalized health recommendation and determine health risks specific to the user's lifestyle challenges and successes. In some examples, the block 120 may determine a relationship by accessing relationship data from an external, cloud-based, or third-party source. For example, a system 100 may download or access NIH, WHO, or other third-party information relating to the relationship between a physiological factor, such as obesity, and a disease, such as a heart disease. In some examples, the data processing block 120 may involve processing of user data, including but not limited to, processing of signals from one or more physiological sensors, a selection of a logging action on a user device, or the like or a combination thereof. In some examples, data processing block 120 may involve communicating with an external hardware processor or database to transmit or retrieve predicted logging actions, a health recommendation, or other output of a system 100. Other data processing may also be possible.

At output 130, the system 100 can include a database storage, display, audible alarm, or other means of conveying, storing, or transmitting data collected by the system 100 or information generated by the system 100. Advantageously, the system 100 may utilize one or more means or devices to output information to a user in order to increase the likelihood that a user interacts with output data of the system 100. For example, an output 130 can include an output device such as a user's mobile device, which a user may be likely to interact with on a consistent basis. In an example implementation, the output 130 can present an efficient GUI to a user 101 providing the user with easy access to one or more logging actions based on the probability that the user will select the logging action.

In some examples, a system 100 may convey, store, or transmit output data from the system 100 through data sharing. For example, user health risks, or raw monitored data may be shared with a third party who has an interest in the health of the user. The third party may be an insurance carrier, an employer, a clinical care provider, or another user. The data may be anonymous or user specific. In some configurations, the sharing may be part of an incentive program for the user, such as a program to lower insurance premiums if the user agrees to participate in the system 100. In other configurations, the sharing may be done as a part of a clinician or social support aspect of the system 100. For example, if a user fails to log their meals for a period of time, the system may share with a designated support user or coach that the support user or coach should check in with the user to ensure they are still complying with the program. Additionally and/or advantageously, the system 100 can share a classification for one or more logging actions based on a user's specific input to the system 100. Further the system can share an ontology such as a classification hierarchy, a listing of logging actions, and one or more models with a third party.

Health Coaching Environment

Figure 2:
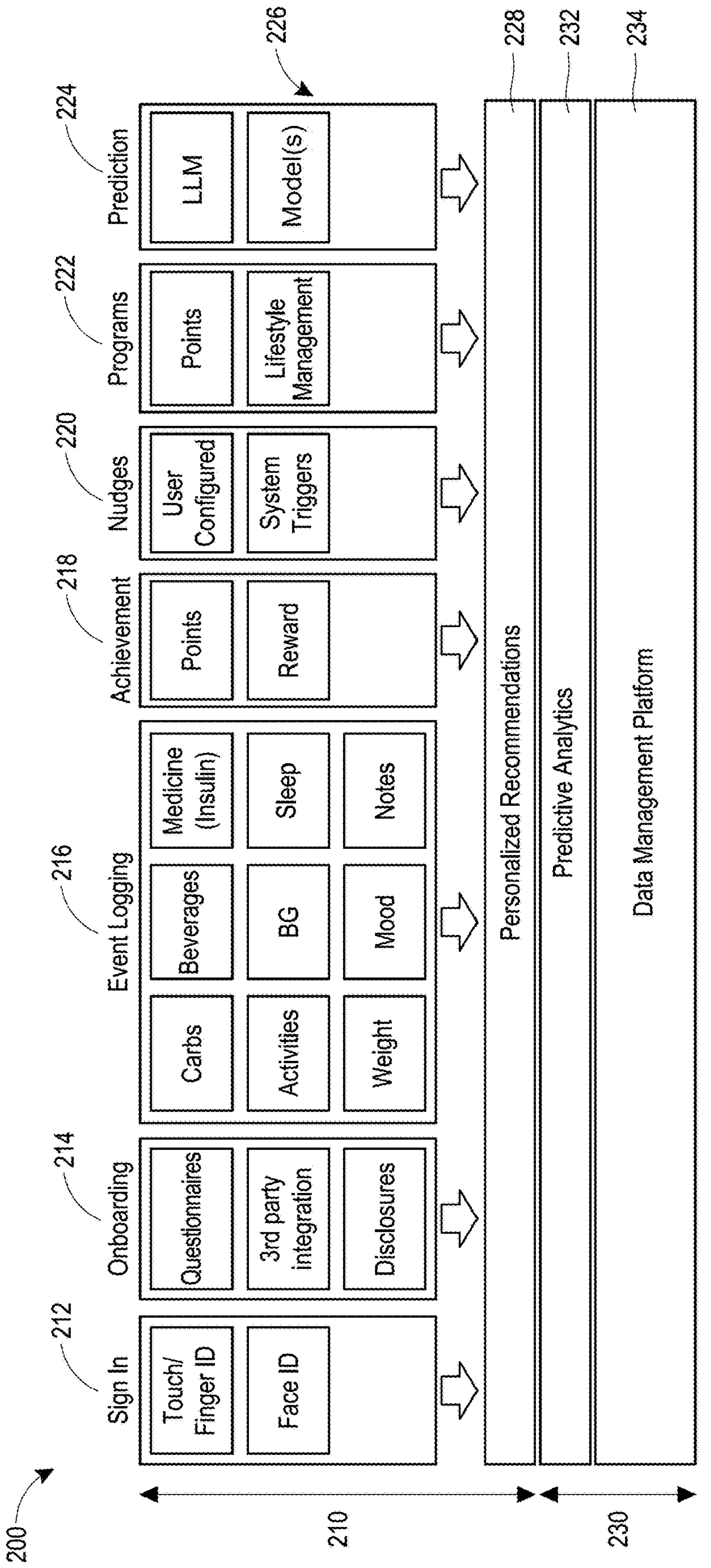
FIG. 2 illustrates an example software environment for a health system.

A system 100 may utilize some combination of interactive application and backend platform to provide health and lifestyle coaching to a user 101. FIG. 2 illustrates an example software environment 200 that may include an application 210 and a platform 230 for a system 100. The application 210 can include one or more interactive elements that may be integrated with a GUI. The one or more interactive elements may include, but is not limited to, a number of coaching modules 226, which provide data to one or more data modules or the platform 230. In some examples, the one or more data modules can include, but is not limited to, a recommendation module 228, an analytics module 232, and a data management platform 234. The data modules can be included in the application 210 or the platform 230.

The coaching modules 226 can include modules for acquiring, analyzing, and outputting data. For example, the coaching modules 226 can include a sign in module 212, an onboarding module 214, an event logging module 216, an achievement module 218, a nudge module 220, a learning program module 222, and a glucose prediction module 224.

The sign in module 212 can include any number of user authentication or enrollment processes. For example, the sign in module 212 can include user authentication methods including knowledge-based authentication, possession-based authentication, inherence-based authentication, location-based authentication, the like, or some combination thereof. In another example, the sign in module 212 can include one or more enrollment processes for registering a user in order to allow the user to access and use one or more aspects of the application 210 and platform 230.

The onboarding module 214 can include any number of means for collecting and processing data relating to the user. The application 210 or the platform 230 can use data from the onboarding module 214 to initialize other modules that may be part of the system 100, such as other coaching modules 226, recommendation module 228, or analytics module 232. The onboarding module 214 can include one or more data collection processes for receiving information directly from the user or third parties. For example, the onboarding module 214 can include questionnaires, forms, or other disclosures in which a user or another party can input data. In another example, the onboarding module 214 can include processes for collecting data from user devices, such as a mobile device, digital scale, smart watch, fitness tracker, glucose monitor, or other device capable of measuring physiological parameters associated with the user. In another example, the onboarding module 214 can include processes for integration with third party applications or for collecting third party data associated with the user. The third-party application integration can include integration with applications that track and collect user data, such as food logging applications, shopping applications, weight tracking applications, healthcare applications, location mapping applications, or other applications that collect user data. In some implementations, the onboarding module 214 can include a bootstrapping process as described below, to assist the health system 100 in developing a customized ontology of the user. The customized ontology can include a hierarchy of classifications to improve the efficiency of a GUI and reduce the average number of presses by a user.

The event logging module 216 can include any number of processes for collecting, storing, and processing user data. The application 210 or the platform 230 can use data from the event logging module 216 in other modules that may be part of the system 100, such as other coaching modules 226, recommendation module 228, or analytics module 232. The event logging module 216 can include one or more data collection processes for receiving information directly from the user or third parties. For example, the event logging module 216 can include questionnaires, forms, or other disclosures in which a user or another party can input data. For example, the event logging module 216 can include a diary, form, questionnaire, chart, table, or other data log for a user, a user's device, another party, or application to input one or more parameters (i.e., logging actions) associated with the user, such as for example, one or more logging actions and/or one or more classifications as described herein. In another example, the event logging module 216 can include processes for accessing one or more parameters associated with the user that may be recorded by a device, such as a blood glucose monitor, heart rate monitor, a mobile device, digital scale, smart watch, fitness tracker, or other device capable of measuring physiological parameters associated with the user. In another example, the event logging module 216 can include processes for integration with third party applications or for collecting third party data associated with the user. The third-party application integration can include integration with applications that track and collect user data, such as food logging applications, shopping applications, weight tracking applications, healthcare applications, location mapping applications, or other applications that collect user data.

The one or more parameters logged by the event logging module 216 can include data related to the physical health, mental health, food intake, activity, mood, or other parameter that can relate to the health or wellbeing of the user. For example, parameters can include carbohydrate intake, beverage intake, medicine intake (for example, insulin), activity, sleep, blood glucose values, weight, mood, notes, some combination thereof or the like. Additionally, a parameter can include a classification (i.e., data associated with the parameter and/or logging action) as described herein.

The achievement module 218 can include any number of processes for tracking, rewarding, or monitoring achievements associated with a user's progress in one or more aspects of a system 100. For example, as described below, a system 100 can include goals, achievements, rewards, points, or other metrics to encourage a user to continue engagement with the system 100. The achievement module 218 can include one or more processes to alert a user of the system 100 to failed or successful achievement of a goal that may be part of the system 100. The achievement module 218 can include one or more processes to track achievements of one or more goals that may be part of the system 100. For example, achievement module 218 can include a point system to track achievements. The achievement module 218 can include one or more processes for rewarding one or more achievements of a goal that may be part of the system 100. For example, the processes for rewarding can include unlocking features of the user application 210, providing monetary rewards or discounts to the user, or facilitating user access to other incentives or rewards.

The nudge module 220 can include any number of processes for encouraging a user to follow one or more aspects of a system 100. For example, as described below, a system 100 can have interactive elements to encourage a user to continue engagement with the system 100. The encouragement can include alerts or other interactions with the user or other party, such as a health care provider. The nudge module 220 can include triggers for the interactive elements. The triggers can be configured to initiate an interaction with the user, such as an alert, encouragement, persuasion, some combination thereof or the like. The triggers can be user configured or built into the application 210. The triggers can be based on data associated with other coaching modules 226, recommendation module 228, analytics module 232, the event logging module 126 or other data associated with the user. For example, a trigger may be configured to interact with a user where the nudge module 220 (or other coaching module 226) determines that a user has failed to log a parameter as part of event logging module 216 within a determined period of time. For example, if a user has not logged their food in the past week, the nudge module 220 may send an alert to the user. In another example, a trigger may be configured to send an encouragement to a user to complete an education module that may be part of a learning module 222.

The program learning module 222 can include any number of interactive elements to provide or engage a user with educational materials. The educational materials can include interactive learning modules, videos, articles, or other multimedia associated with a system 100. The educational materials can include any number of learning materials that may be successively or otherwise released to the user regarding aspects of the system 100 or the user's health. For example, the educational materials can include diabetes prevention materials, lifestyle management materials, heart disease prevention materials, or other health related educational materials.

The prediction module 224 can generate and use any number of predictive models related to analyzing data associated with the system 100. For example, the prediction module 224 can determine one or more habits of a user, and/or the like. The prediction module 224 can include one or more predictive models configured to predict the next logging action a user might select based on a probability of, among other inputs, previously selected logging actions. The one or more predictive models of the prediction module 224 can include the combination of (chaining together of) one or more AI models, Large Language Models (LLM), and machine learning algorithms to predict and/or analyze patterns and habits of an individual user and/or a group of users. Further, the prediction module 224 can include any number of methods for validating a newly generated predictive model. In one example implementation, the prediction module 224 can validate one or models for accuracy by comparing the weighted sum of the logging actions for the one or more generated models to a threshold weighted sum.

The prediction module 224 can further include one or more constraints. For example, the one or more constraints can include at least one filter to exclude newly generated models that yield marginal improvement but require substantial user interface changes. Constraints can also include a rule defining how one or more inputs to a model can be combined, or the inclusion of an LLM for predicting a next word of a logging action and/or a classification based on a user input.

Data from the one or more coaching modules 226, which can include data from the sign in module 212, onboarding module 214, event logging module 216, achievement module 218, nudge module 220, learning program module 222, and prediction module 224 can be utilized by some combination of the recommendation module 228, the analytics module 232, or the data management platform 234.

The recommendation module 228 can include any number of processes to recommend an action designed to improve the user's health. For example, as described below, a recommendation module 228 can include processes for analyzing user data, determining recommendations based on the user data, or other processes related to recommending user or healthcare provider actions to improve a user's health.

The analytics module 232 can include any number of processes to analyze user data and to make predictions about a future event associated with the user. For example, as described below, the analytics module 232 can include a process to predict a future health condition of the user based on the user data from the one or more coaching modules 226. The prediction can include any number of statistics, risks, models, or other predictive data associated with the health of the user. Output from the analytics module 232 can be output to the user, used to generate recommendations with the recommendation module 228, or used with the one or more coaching modules 226.

The data management platform 234 can include any number of processes for collecting or managing data. For example, the data management platform 234 can include processes for gathering, managing, storing, organizing, and analyzing data. The data management platform 234 can include algorithms to process user data from one or more sources of information using artificial intelligence or other big data algorithms.

Example Data Processing

Figure 3:
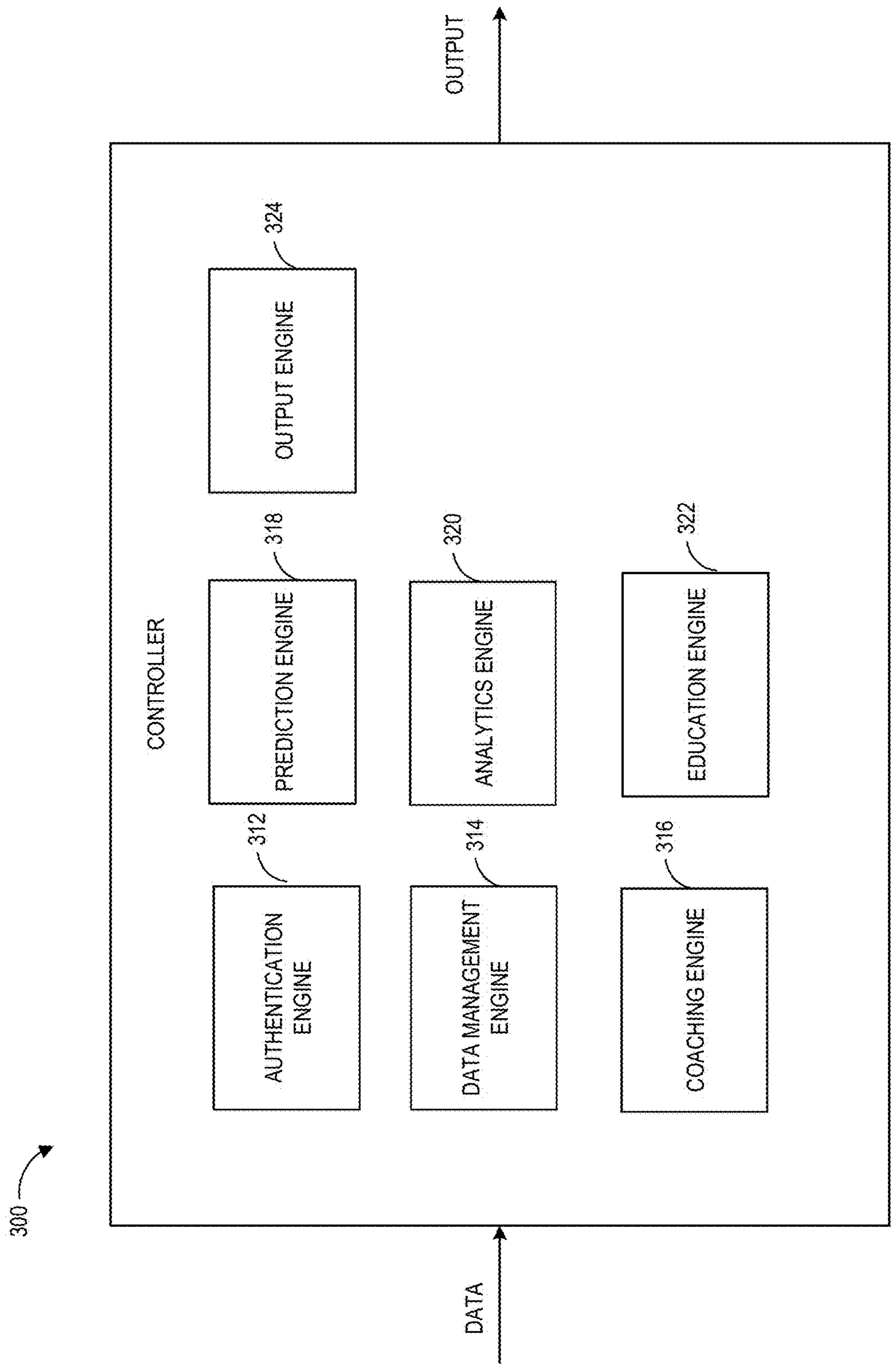
FIG. 3 illustrates an example controller to collect, process, and output user data.

The system 100 can include a controller 300 for collecting, processing, and outputting data. For example, the controller 300 can operate the coaching modules 226, recommendation module 228, analytics module 232, or data management platform 234 using one or more software engines. The controller 300 can operate the engines using one or more hardware processors. The one or more hardware processors can be local hardware processors (for example, on a user mobile device) or remote hardware processors (for example, on a remote server). FIG. 3 illustrates an example controller 300 to collect, process, and output user data. The controller 300 can include an authentication engine 312, a data management engine 314, a coaching engine 316, a prediction engine 318, an analytics engine 320, an education engine 322, and an output engine 324.

An authentication engine 312 can include one or more processes for authenticating a user. The authentication engine 312 may operate in conjunction with the sign in module 212 or other coaching modules 126 as discussed with reference to FIG. 2. The authentication engine 312 can register or verify a user's identify for the purposes of accessing aspects of the system 100. For example, the authentication engine 312 can verify a user's identity to secure access to a user's health data that may be accessible within the system 100. The authentication engine 312 can register or verify a third party's credentials to access or edit user data. For example, a third party may be a health care provider. The authentication engine 312 may verify the third party's credentials to allow the health care provider to access a user's data, such as a food or activity log.

A data management engine 314 can include one or more processes for processing, storing, or accessing data acquired by the system 100. For example, the data management engine 314 can process signals for analysis by the controller 300 from physiological sensors monitoring a user. In another example, the data management engine 314 can access, store, or edit user data from a variety of data sources, such as user logs, user tracking devices, third party sources, or other sources of user data. In one implementation, the data management engine 314 can determine one or more classifications of a logging action based on an ontology stored in a database. The database can be stored locally and/or sourced from a third party as described herein. In one implementation, an ontology referenced by the data management engine 314 can be based on hypernyms, and/or a classification hierarchy. The data management engine 314 can operate in conjunction with other modules of the application 210, such as the sign in module 212, onboarding module 214, event logging module 216, the prediction module 224 or other coaching modules 126, such as discussed with reference to FIG. 2.

A coaching engine 316 can include one or more processes for interacting with a user. For example, the coaching engine 316 can include processes for recommending behavioral or other changes to a user based on user data. In some configurations, the coaching engine 316 can provide feedback to the user based on the user data or the recommendations. As described below, the feedback may take the form of encouragements (or nudges), or rewards designed to push the user to improve their lifestyle or follow the recommendations.

In some configurations, the coaching engine 316 can provide a recommendation that includes a regimen of educational materials and user specific behavioral recommendations based on user health risks or user capabilities. For example, if a health risk determined by analytics engine 320 is that the user is at a 75% risk of type 2 diabetes, the system may recommend, among other things, a set of interacting diabetes learning modules for the user to interact with as well as a new diet that cuts out refined sugars. However, if the user were to indicate that they had a recent hip replacement, the system may not recommend a regimen of intense cardio, but rather a regimen of light walking as a means of increasing exercise level.

In some configurations, the coaching engine 316 can provide feedback based on triggers. The triggers may be identified by the system 100, user, or third party. For example, the system 100 may identify specific activities that result in poor lifestyle choices and send feedback to the user designed to push the user to make change to those activities. For example, the system 100 may identify that where a user skips a meal, the user eats more foods with high sugar content during the subsequent meal time than they would if they did not skip a meal. The coaching engine 316 may provide feedback to the user in the form of an alert to eat if the system 100 identifies the skipped meal trigger.

In another example, the coaching engine 316 can provide feedback based on a user's compliance with a recommendation. The coaching engine 316 may provide encouragements or rewards to comply with a recommendation, identified goals, or when a user achieves an achievement. For example, the coaching engine 316 can provide third party rewards, provide monetary rewards or discounts to the user, or facilitate user access to other incentives or rewards.

A prediction engine 318 can include any number of processes for analyzing and predicting user physiological parameters or behaviors. For example, as discussed below, the prediction engine 318 can include processes to predict a user's blood glucose based on a user's recorded data. In another example, the prediction engine 318 can include processes to predict a user's lifestyle behaviors based on a user's recorded data. In particular, the prediction engine 318 can determine that a user may purchase unhealthy foods if a user is located at a fast food location. In a further example, the prediction engine 318 can determine a probability that a user will select each logging action within a database of logging actions. The prediction engine 318 can base this prediction on, for example, an entropy model for the logging actions as part of the event logging module 216. The entropy model can be generated using an ontology as described herein. The result of the prediction engine 318 can be, for example, a set of instructions to display one or more logging actions to reduce the total number of presses the user must make on a GUI to log an action. The prediction engine 318 can operate in conjunction with, for example the prediction module 224, the programs module 222, the event logging module 216 and/or any other module discussed herein.

The prediction engine 318 can further utilize one or more LLM to predict a user's next word while attempting to log an action. Additionally and/or alternatively, the prediction engine 318 can use an LLM to determine one or more classifications of a logging action, for example, by receiving a logging action and generating one or more prompts, requesting that the user select one or more suggested classifications for the selected logging action. The prediction engine 318 can include processes utilizing one or more LLMs to support the generation of a custom ontology based on a specific user's most frequently selected logging actions and a previously referenced classifications hierarchy. For example, a list of logging actions can be utilized during the onboarding process, where a GUI displays a list of logging actions and requests that the user answer one or more questions regarding classifications of the logging action.

An analytics engine 320 can include any number of processes for analyzing user data and determining health risks associated with the user data. The analytics engine 320 can calculate health risk by analyzing the user data in the context of identified health risk factors. For example, the analytics engine 320 may compare the user data to health risks recognized by health authorities, such as the WHO or the CDC, risks identified by the system 100, or risks identified through AI analysis of a database of users. Recognized risks within user data may be flagged for the user or used to calculate health scores. For example, where the user data indicates that the user has an obese BMI and an elevated HbA1c, the system may calculate a risk of diabetes at 70%. The analytics engine 320 may use this risk to calculate a health score on a set scale or as a means to calculate a recommendation for improvement. However, mitigating factors may also be identified in user data and used within the health score calculation. For example, a user may have an obese body mass index (BMI), but a resting heart rate of 45 beats per minute. The fact that the user has a lower resting heart rate may be utilized in the health risk calculation to mitigate the increased risk for cardiovascular disease that is recognized with an increased BMI because the user's resting heart rate indicates a healthy heart despite the BMI.

An education engine 322 can include any number of processes for providing a user access to educational materials. The education engine 322 can provide access to different types of educational materials based on user data. For example, the controller 300 can determine that a user has a high risk for diabetes. The education engine 322 can provide access to diabetes educational materials. The education engine 322 can provide access to educational materials as part of an educational course. For example, the education engine 322 can provide educational materials that are part of a ten-week educational course on lifestyle management. The education engine 322 can release a series of educational materials on a periodic basis or based on a user interaction with the educational materials. For example, the education engine 322 can provide a user access to educational materials where the user receives a passing score on quizzes or tests associated with the system 100.

The educational materials can include interactive learning modules, videos, articles, or other multimedia associated with a system 100. The educational materials can include a number of learning materials that may be successively, collectively, or otherwise released to the user regarding aspects of the system 100 or the user's health. For example, the educational materials can include diabetes prevention materials, lifestyle management materials, heart disease prevention materials, or other health related educational materials.

An output engine 324 can include any number of processes for outputting data to a user, a user device, third party, third party device, or database. For example, the output engine 324 can output data collected, accessed, analyzed, or generated by the system 100, such as health risk, recommendations, physiological parameter predictions, user data logs, a request for a logging action based on a prediction of the user's most probable logging actions, or other data associated with the user. The output engine 324 can output data based on any number of criteria. For example, data may be output periodically, continuously, or on demand. Access to the output data may be provided as a matter of course for authenticated users, for a fee, or as part of an incentive program for the user.

Example Health Coaching System Authentication Process

In some examples, a coaching system 100 may facilitate access to user data or other content based on user credentials. For example, a user may be granted credentials associated with a level of access to aspects of a coaching system 100. In some examples, different types of users may have different levels of access. For example, there may be a patient user, a healthcare user, a third party user, or other users. A patient user may be a user about whom data is collected or to whom recommendations or other output data is directed. A healthcare user may be a user who may be involved in treating or managing a patient user's healthcare, such as a doctor, nurse, coach, support user, or the like. A third party user may be a user involved in managing the system 100, a user granted access to view or otherwise edit data within the system 100 by another user, such as a patient user or healthcare user, or another user. In some examples, a user may be granted a level of access to edit, view, or otherwise control or access data or features of an application 210 based on a user type, user capacity, the like or a combination thereof. For example, a child user may be granted a lower level or different level of access to application features or editing access than an adult user. In some examples, different features may be accessible to a user based on the credentials.

Figure 4:
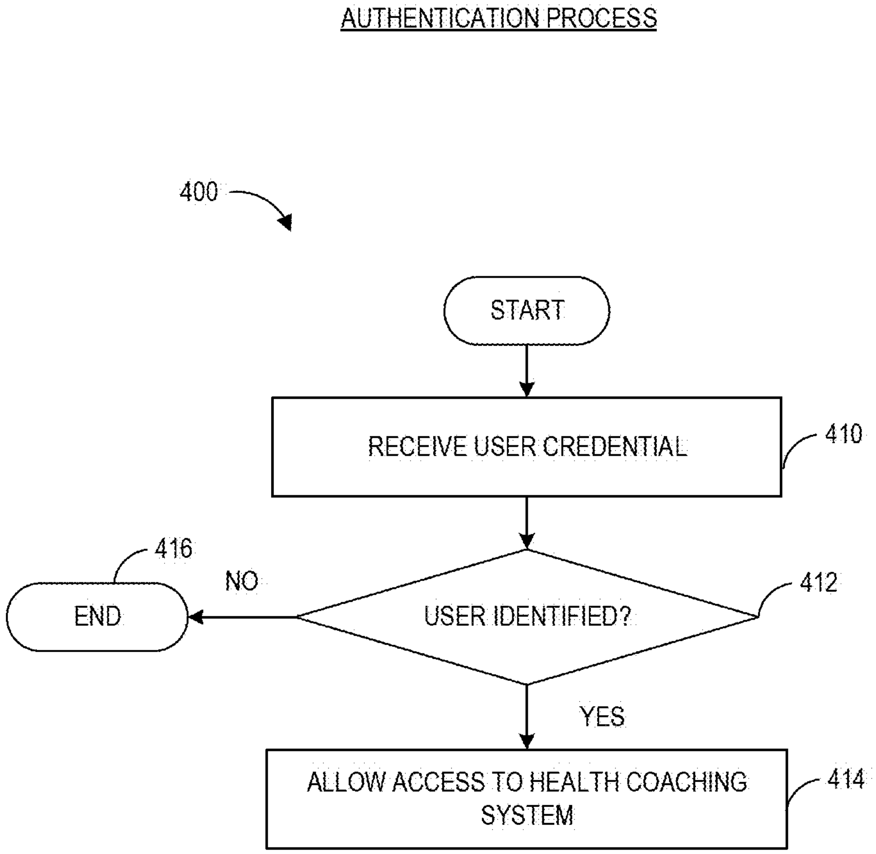
FIG. 4 illustrates an example authentication process that may be part of a health system.

In some examples, the controller 300 can operate an authentication engine 312 that can include one or more processes for authenticating a user. FIG. 4 illustrates an example authentication process 400 that may be part of an authentication engine 312. For example, the authentication process 400 can include a credential receiving block 410, an identification block 412, an access block 414, and an end block 416.

At credential receiving block 410, a controller 300 can receive one or more credentials associated with the user or a third party. The credentials can include one or more authentication factors, including but not limited to knowledge-based factors, possession-based factors, inherence-based factors, location-based factors, the like, or some combination thereof. Knowledge-based factors can include but are not limited to password, pin, or other security information factor. Possession-based factors can include but are not limited to password tokens, ID cards or fobs, or other item that a user may need to possess in order to log in. In some examples, possession of a user device, such as a glucose sensor, may provide an indication of a patient credential. For example, a glucose sensor may be paired to a user's mobile device. The glucose sensor may provide a unique identifier to the coaching system 100 to identify that a user wearing the glucose sensor is an authenticated user. Inherence-based factors can include but are not limited to biometric factor, such as iris codes, fingerprints, facial recognition, or voice recognition. Location-based factors can include but are not limited to the physical or digital address of a user.

At an identification block 412, the controller 300 can analyze the one or more credentials from block 410 to determine if the credentials match an authorized set of credentials. For example, an authorized set of credentials can include an authorized passcode, biometric ID, authorized location, or other credential associated with a recognized user of the system. If the controller 300 determines that the credentials match the authorized set of credentials, the controller 300 may allow the user access at a block 414. If the controller 300 determines that the credentials do not match the authorized set of credentials, the controller 300 may refuse access to one or more aspects of the health coaching system at a block 416.

At access block 414, the controller 300 can allow access to one or more aspects of the system 100 based on the credentials. For example, the controller 300 can allow editing access to personalized recommendations if the controller 300 determines that the credentials match a health care provider with editing access. In another example, the controller 300 can allow writing access to user data logs if the controller 300 determines that the credentials match a user enrolled in the system 100. In another example, the controller 300 can allow viewing access to user data if the controller 300 determines that the credentials match an authenticated third party, such as an insurance provider. In another example, the controller 300 may facilitate access to user specific aspects of a system 100. For example, if the credentials match a coach access level, the controller 300 may allow the user to view aspects of the system 100 associated with a health coach as opposed to a patient user, such as a review of a patient user's progress within the system 100 or coach messaging.

Example Data Management Engine

Figure 5:
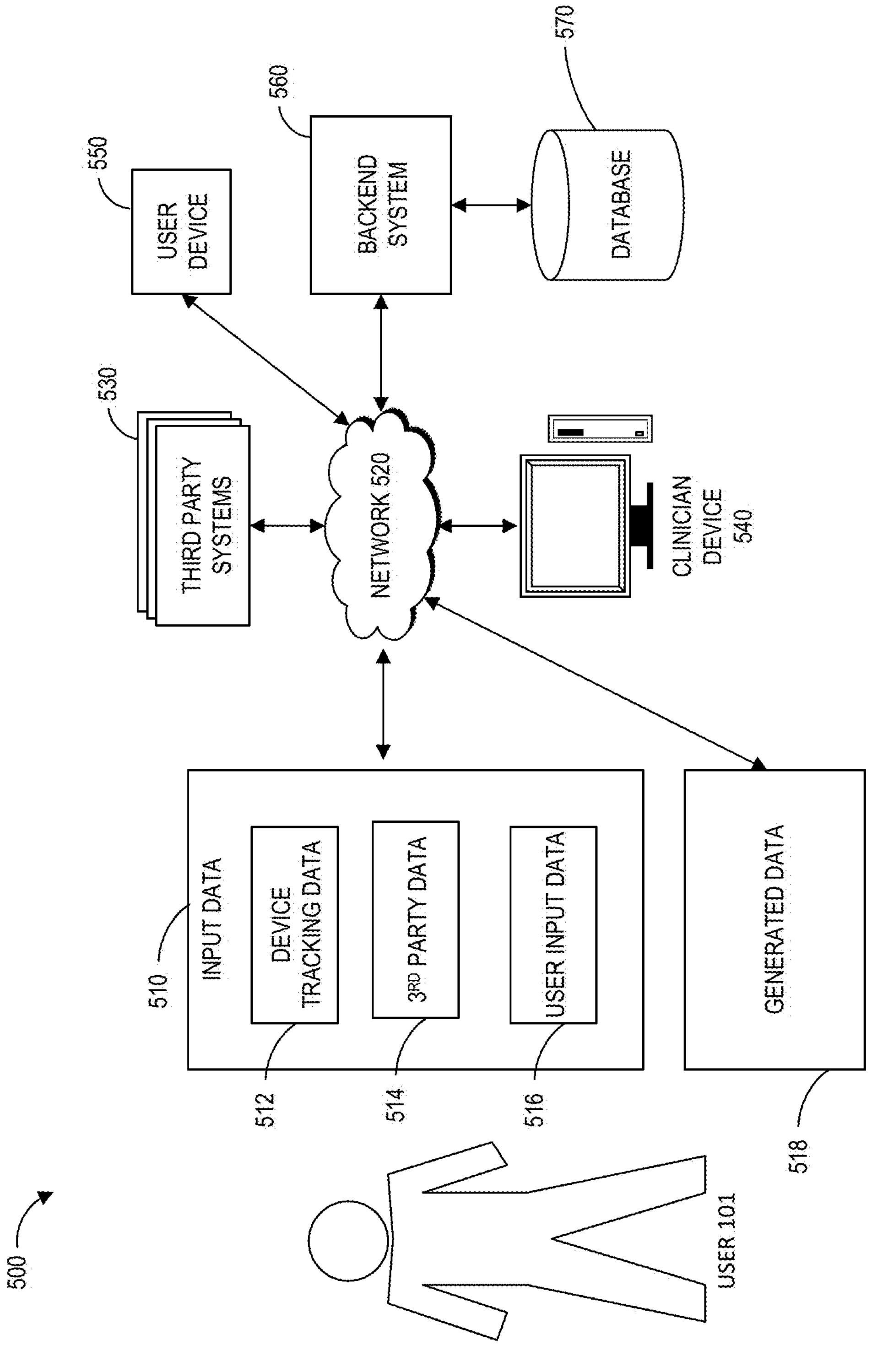
FIG. 5 is a block diagram showing an example data management environment that may be part of a health system.

The controller 300 can operate a data management engine 314 that can include one or more processes for processing, storing, or accessing data acquired by the system 100. FIG. 5 is a block diagram showing an example data management environment 500 that may be part of a data management engine 314. For example, the data management environment 500 can include input data 510 and generated data 518 associated with a user 501, a network 520 a clinician device 540, one or more third party systems 530, one or more user devices 550, a backend system 560, and a database 570.

The input data 510 can include data from any number of sources, including but not limited to device tracking data 512, third party data 514, and user input data 516. Device tracking data 512 can include data gathered by user or other devices. For example, the user 101 may be monitored by physiological sensors or through device applications. The physiological sensors can include any number of physiological sensors that may measure physiological parameters associated with the user, including but not limited to analyte monitors (such as blood glucose monitors, including an SMBG or CGM, or other invasive or non-invasive analyte monitor), scales, pulse oximeters, fitness trackers, smart wearable devices, some combination thereof or the like. The device applications can include mobile device applications that may monitor or track user activity. For example, the device application data can include step counters, location trackers, camera data, or other data from a mobile device.

In some configurations, the system 100 can collect data from devices designed to integrate with the system 100. For example, as described below, the system 100 may utilize a body scale equipped with a variety of sensors that enable the scale to measure user information, such as weight, heart rate, heart rate variability, height, Body Mass Index (BMI), waist circumference, the like, or some combination thereof. In another example, the system 100 may utilize a glucose monitor equipped to measure blood glucose of the user. The system 100 may communicate with a device to track health metrics at certain intervals or provide prompting to the user to engage with a device in order to measure metrics. In the case of a glucose monitor, the system may prompt a user to measure their glucose using the glucose monitor at certain times, such as after food intake or at intervals during the day.

An input device may connect to a hardware processor associated with system 100. For example, the input device may collect device tracking data 512. The input device may wirelessly or with wires transmit the device tracking data 512 to a hardware processor associated with a user's mobile device 550 or to a backend system 560. In some configurations, the input device may optionally connect to the user device 550 or backend system 560 over a network 520.

Third party data 514 can include data from any number of external sources of data related to the health of the user 101. For example, the third party data 514 can include, but is not intended to be limited to, medical data, hospital data, or user activity data from third parties. The third party data may be obtained through direct third party interaction with the system 100 (for example, through manual clinician input) or through a connection with a third party database.

Third party data 514 can include medical data collected by a third party. The medical data can include data from a user's medical history that has the potential to affect the current or future health of the user 101, such as medication history, treatment history, family history, or the like. The medical data can be accessed or retrieved from any number of sources, including but not limited to information from clinical visits, previous laboratory work, genetic testing results, or other sources of historical medical data. For example, medical data can include information obtained by clinicians regarding the health of the user 101 during a medical appointment or hospital admission, such as vital sign measurements, diagnosis information, treatment plan information, or the like.

Third party data 514 can include user activity data collected by a third party. As described below, the user activity data can include data related to an activity or health of the user 101. The user activity data can include data related to the shopping, exercise, eating, social, or other activities of the user. For example, a user may use a particular grocery chain for their food needs. The grocery chain may track the user's food purchases. The food purchases may be used as third party data by the data processing block 120. In another example, the user's shopping habits may be tracked through the use of their credit or debit cards by their bank or credit card company. Those purchases may be used as third party data by the controller 300.

In some examples, third party data 514 may be collected or stored in cloud based storage associated with the system 100. A controller 300 may be configured to authenticate the collected third party data 514 or other data using the third party data 514. For example, a controller 300 may be configured to corroborate a user input with third party data 514, such as electronic medical record data. For example, a user input may indicate that they have type 1 diabetes. The controller 300 may validate this information by accessing electronic medical record data (EMR) data to detect if type 1 diabetes has been diagnosed for the user. If the controller 300 determines that an input is incorrect or invalid, the controller 300 may notify the user, limit access to one or more aspects of the application or system 100, attempt to re-validate, or perform another action, such as described herein. If the controller 300 determines that an input is valid, the controller 300 may or may not notify the user, facilitate access to aspects of the application or system 100 (for example, appropriate educational modules), prompt a user for further inputs, or perform another action, such as described herein.

User input data 516 can include data from the user 101 that relates to the health of the user 101. For example, the user input data 516 can include but may not be limited to lifestyle information such as activity information, location history, sleep information, food intake information, shopping information, or other user lifestyle information (e.g., one or more logging actions). The user input data 516 can be obtained through manual input as prompted by the user or components of the system 100. For example, a GUI may display a series of health-related questions at the start of the program that the system 100 can periodically prompt the user to update if appropriate. This approach is particularly advantageous to use for historical user information, such as medical history and medical genetic markers. For example, a user may start the program with a broken wrist. The user may input this information and the controller 300 may facilitate upload of this information to a database that the system 100 or controller 300 is configured to access or communicate with in order analyze information or to provide recommendations. In some examples, the controller 300 may validate the input with third party data. In some examples, the system may use this information to provide recommendations based on the information. For example, the controller 300 may provide exercise recommendations based on the user input recommendations, such as exercises designed to help avoid aggravating the user's broken wrist. Additionally, the system may prompt the user to update the database about the status of their ongoing health issues. For example, the system may ask the user about the current status of their broken wrist at periodic intervals in order to update user recommendations.

Additionally, and/or advantageously, the user input data 516 can include one or more logging actions and/or one or more classifications associated with at least one logging action. The user input data 516 can further include requests to update an ontology associated with one or more logging actions and classifications.

Generated data 518 can include data generated by one or more engines, such as authentication engine 312, coaching engine 316, education engine 322, prediction engine 318, or analytics engine 320.

The controller 300 can optionally process the input data 510 or the generated data 518 to store, analyze, normalize, or otherwise process the input data 510 or the generated data 518 for further analysis by the controller 300. For example, the controller 300 can compress the input data 510 for storage in a database 570. The controller 300 can output the input data 510 or generated data 518 to a user device 550. The user device 550 or controller 300 may transmit data to a backend system 560 (such as a remote server or cloud server) over a network 520. The user device 550, the backend system 560, and other devices can be in communication over the network 520. In some cases, the user device 550 can download processed data from the backend system 560 after the controller 300 transmits the input data 510 or generated data 518 to the backend system 560 for further processing. These other devices can include, such as in the example shown, a clinician device(s) 540, and third party systems 530. However, more or fewer devices may access the input data 510 or generated data 518 with other systems or devices. The controller 300 can enable a user and others (such as clinicians) to monitor various aspects related to the user's data, such as food logs, activity logs, recommendations, or health risks that may be generated by the system 100.

Example Functionality of the Health Coaching System

Figure 6:
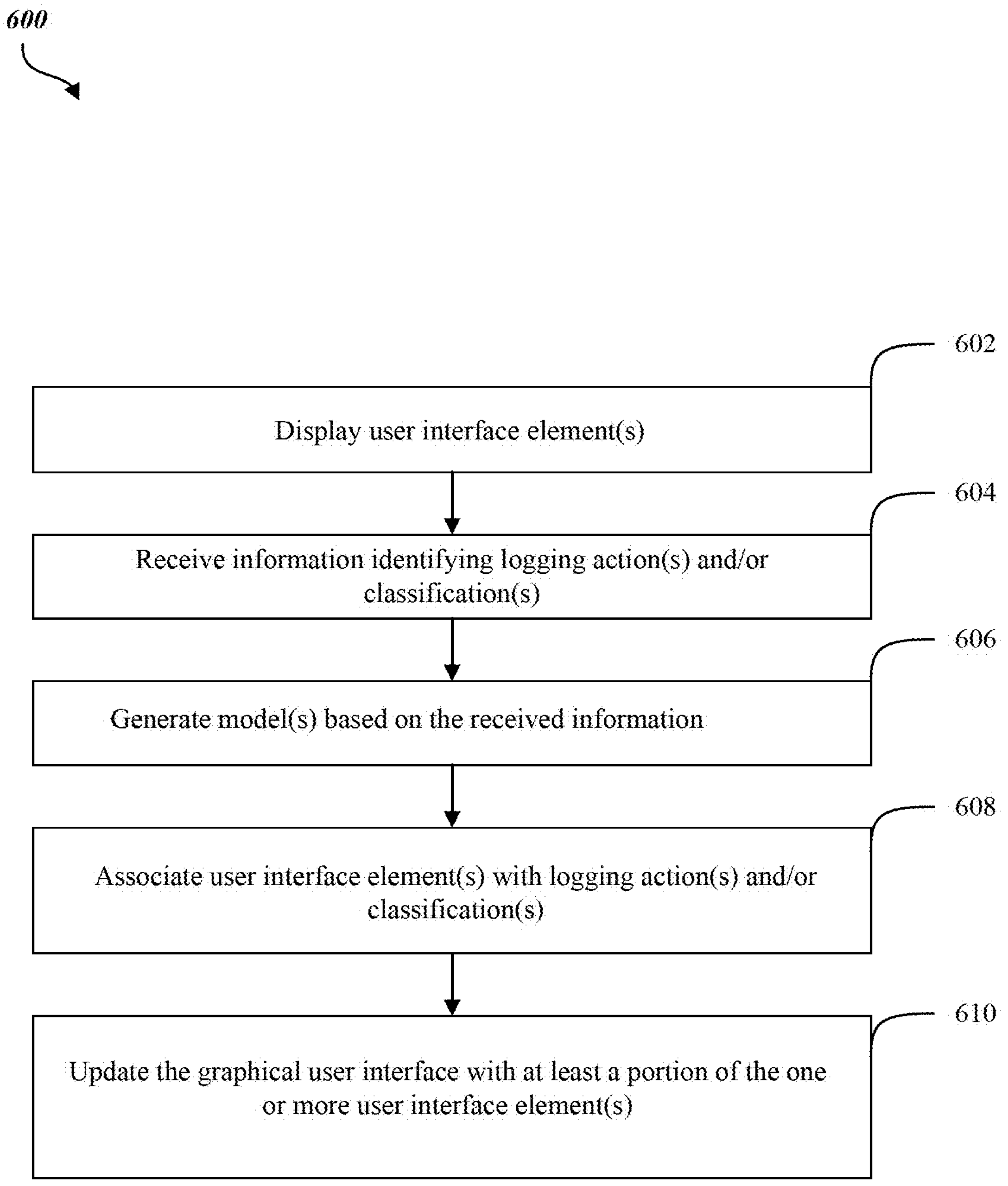
FIG. 6 is a flow chart depicting an example routine for updating a GUI based on a user input.
Figure 7:
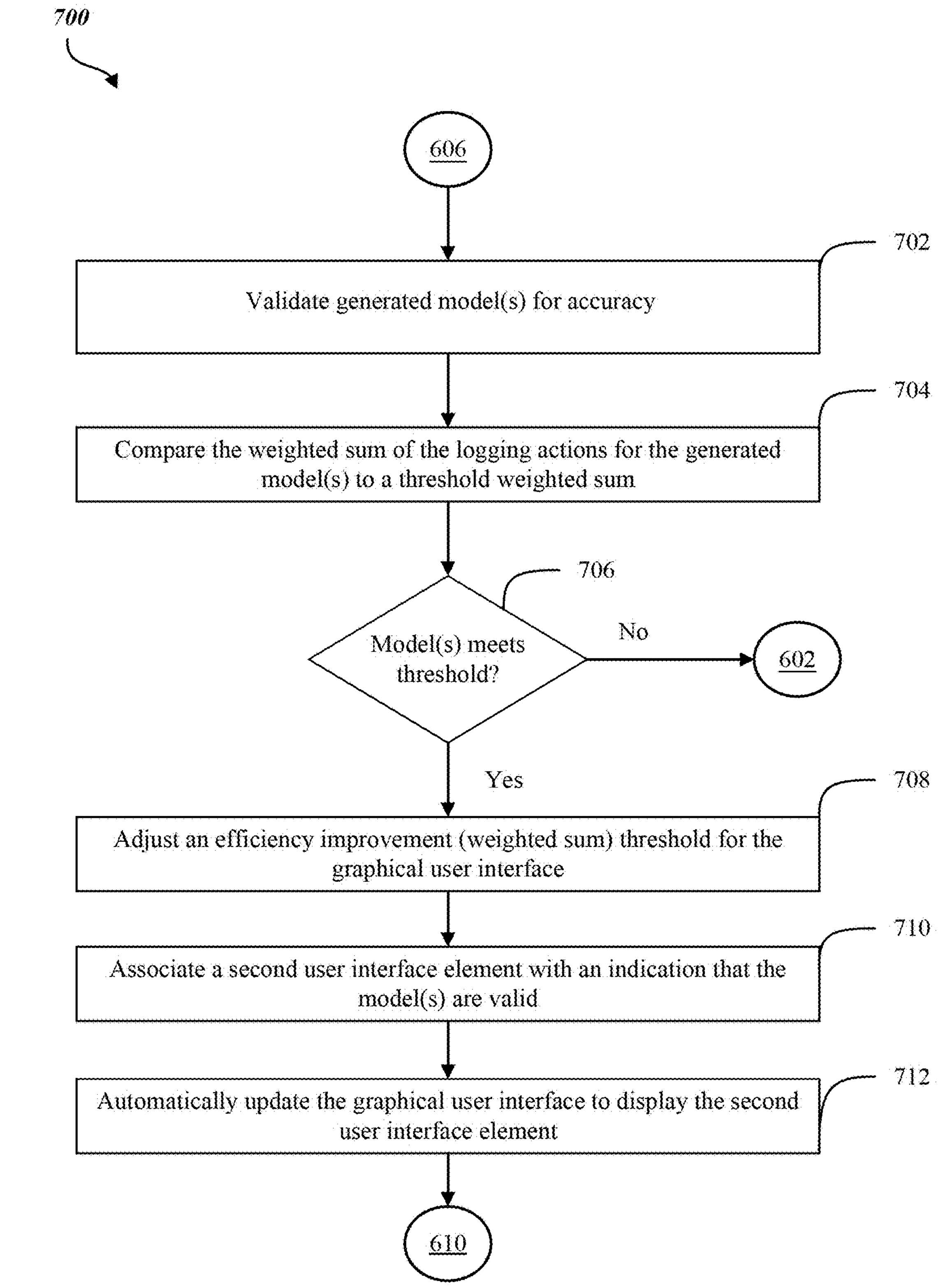
FIG. 7 is a flow chart depicting an example routine for validating one or more models before applying the models in production.

FIGS. 6-7 show flow charts illustrating example operations of the system 100 (and/or various other aspects of the example data management environment 500), according to various embodiments. The blocks of the flow charts illustrate example implementations, and in various other implementations various blocks may be rearranged, optional, and/or omitted, and/or additional block may be added. In various embodiments, the example operations of the system illustrated in FIGS. 6-7 may be implemented, for example, by the one or more aspects of the system 100, various other aspects of the example data management environment 500, and/or the like.

FIG. 6 is a flow chart depicting an example routine 600 for updating a GUI based on a user input. At block 602 the system 100 displays one or more user interface elements on a GUI. The one or more user interface elements can be associated with one or more logging actions and one or more classifications. Logging actions and associated classifications can be generated from any of the means as describe herein, such as for example, by the event logging module 216, the prediction module 224, the prediction engine 318, and/or any of the modules and engines as described herein. The logging action and/or classifications associated with the user interface elements can be, for example, a listing of one or more physical activities and/or items of consumption as discussed herein. The listing of logging actions presented to the user can be generated by the system 100, and/or based on one or more databases accessed by the system. The one or more databases can be located on a third-party server and/or hosted locally as described herein. The system 100 may determine which logging actions to display based on one or more models. The one or more models can be, for example, a trained AI model configured to reference an ontology to predict the probability that a user may select one or more logging actions. The logging actions can be displayed for example, in order of most to least likelihood that a user will select the logging action.

At block 604, the system 100 receives information identifying a logging action and at least one classification associated with the logging action. The information can be received via, for example, a user input on a GUI as displayed via the event logging module 216 and/or another module described herein. Additionally, the data management engine 314, the prediction engine 318, the analytics engine 320 and/or another engine may receive the information identifying a logging action and at least one classification. The logging action and classification can be, for example, received before, during, or after a user has consumed an item and/or completed a physical activity. In an example use case, a system 100 can receive one or more user selected logging actions, for example, that a user has consumed water and two slices of cheese pizza. Further, the system 100 can receive one or more classifications for the pizza and/or any other classification, such as that the cheese pizza was from a local vendor and/or a chain retailer and/or any other characteristics about the pizza (e.g., thin crust, extra cheese, garlic bread crust, wheat crust, extra sauce, or the like). Additionally, one or more classifications may be generated by the system 100 when a logging action is selected. For example, a time and/or location for a selected logging action.

At block 606, the system 100 can generate and/or update one or more models based on the received logging actions and/or classifications. The one or more models can be generated by, for example, one or more processes as determined by the prediction module 224, the prediction engine 318 and/or another portion of the system 100. Additionally, the logging actions and/or classifications may be transmitted to a third party, where the third party is configured to generate and/or update one or more models.

One or more models can be generated to display the most probable logging action based on input form, for example, one or more previously selected logging actions. Additionally, the one or more models can use an ontology, such as a classification hierarchy to determine which logging actions to display. The output of the one or more models can include a probability distribution based on one or more logging actions and/or classifications stored in a database and accessed by the system 100. The probability distribution can be created by assigning a probability to each logging action based on the weighted sum of a likelihood that a user will select at least one logging action from the one or more logging actions. The output of the trained model can be a listing of logging actions that a user may select from most probable to least probable. Additionally, and/or alternatively, the output can be a combination of logging actions and classification, where the combination of logging actions and classifications are configured to minimize the average number of presses required by a user when selecting a next logging action. Additionally, one or more models can be validated by the system 100. Model validation will be described as part of FIG. 7 below.

At block 608, the system 100 can automatically associate one or more user interface elements with one or more logging actions and one or more classifications based on the assigned probability of each logging action.

At block 610, the system 100 can update the GUI to display at least a portion of the updated one or more user interface elements. The updated GUI can display the logging actions and/or classifications based on the output of the one or more models. Advantageously, the updated GUI can provide the user with an easily accessible and efficient GUI. The efficient GUI can reduce the number of clicks required to select a logging action by presenting to the user, a listing of logging actions the user is most likely to select. Additionally, the system 100 can enable a user to efficiently navigate a list of logging actions by determining and displaying one or more classifications along with the suggested logging actions to efficiently guide the user through the listing of logging actions to select a logging action with the least number of presses on the GUI. The routine 600 ends after the system 100 updates the GUI with a display of one or more user interface elements.

FIG. 7 is a flow chart depicting an example routine 700 for validating one or more models before applying the models in production. The validation process can be executed as part of, for example, the data management engine 314, and analytics engine 320, the prediction engine 318 and/or any other engine and/or module as described herein. The routine 700 begins at block 606. At block 606, the system 100 generates one or models as described with reference to FIG. 6.

At block 702, the system validates the one or more models for accuracy. The models are validated before being used to update a GUI to minimize the average number of presses for a user to log an action. Models are validated to determine whether the newly generated models provide a sufficient improvement in comparison to one or more previous models. Additionally, models are validated as a sanity check before implementation, to prove that the models will improve the overall user experience and increase the efficiency of selecting one or more logging actions prior to using the models in production. The models are validated prior to automatically associating the one or more user interface elements of a GUI with logging actions based on the models output.

At block 704, the system 100 compares the weighted sum of the user's selected logging actions for the one or more generated models to a threshold weighted sum. A weighted sum can include the sum of an assigned weight for one or more logging actions and/or one or more classifications. For a generated model, the system 100 can assign a weigh to each logging action. The weight can be assigned based on, for example, the frequency that a logging action is selected by the user. The period used to determine a selection frequency can be any time period, such as an hour, day, week, month, year, or the like. The frequency can be any number of times a logging action is selected by the user. For example, 1, 2, 3, 4, 5 or more. In an example implementation, a frequency for water consumption can be 8 times per day.

The system 100 can include a multiplier used to determine a weight for one or more logging actions. The multiplier can be based on a determined frequency that a logging action is selected. In one implementation, the value of the multiplier can be any value with a range of 0 to 1, for example 1, 0.9, 0.8, 0.7, 0.6, 0.5, 0.4 and the like. For example, if a logging action is recorded within the same day, a multiplier of 1 may be used to determine the weight of the logging action. Likewise, if a logging action is recorded within 7 days, a multiplier of 0.9 can be used to determine the logging action's weight. In some implementations, the multiplier can be any value within a range such as from 0 to 1, 0 to 10, −5 to 5, 4 to 100 or the like. Additionally, a weighted sum can be assigned for one or more of the classifications associated with a selected logging action. Classifications associated with the selected logging action can include a multiplier as well. The multiplier can be dependent upon, for example, the number of times a classification is present for a group of logging actions. For example, two logging actions (i.e., water and milk) may share one or more of the same classifications (such as, for example, beverage, time of day consumed, location consumed, day of week consumed, or the like). The one or more shared classifications may also be associated with a multiplier based on the number of occurrences of the classification within a determined frequency, such as within a day, a week, and/or any other time.

The threshold weighted sum of the model can be a value indicative of a minimal efficiency improvement of the GUI based on a model's output. An efficiency improvement based on a probability distribution can be defined as, for example, the average number of primitive user actions (e.g., clicks, presses, or the like) required to log a logging action. In one implementation, a threshold value can be established based on a combination of logging actions and classifications with a weighted Zhang Shasha tree edit distance of a specific value. Advantageously, a set Zhang Shasha tree edit distance may allow the user to take advantage of muscle memory. Additionally, a threshold based on a tree edit distance can be weighted according to one or more additional requirements. For example, the threshold can be adjusted based on more deeply nested menus (e.g., deeply nested logging actions based on one or more classifications). In a further example, the threshold can be adjusted based on the location of one or more logging actions and/or classification within the window of a GUI, whether the locations are dynamic and/or static, and/or the size and shape of the screen displaying the logging actions and/or classifications.

At block 706, the system 100 determines whether the weighted sum of the model meets or exceeds the threshold value. If the system 100 determines that the generated model meets the threshold value, the routine 700 proceeds to block 708. If the system 100 determines that the calculated efficiency of the generated model does not meet or exceed a threshold value, then the routine 700 proceeds to block 602 of FIG. 6, where the system 100 displays one or more user interface elements based on a previously generated model as described above.

At block 708 the system 100 adjusts an efficiency improvement threshold for one or more portions of the graphical user interface. The efficiency improvement threshold can be any value as described herein. In some implementations, once the system 100 has determined that a generated model has met a threshold value, the system 100 may adjust the benchmark efficiency threshold value such that future models generated by the system 100 may be required to improve the efficiency of the GUI by a predetermined margin. Advantageously, adjusting an efficiency improvement threshold after a model has met the threshold will enable the system 100 to incrementally improve the efficiency of the GUI.

At block 710, the system 100 associates a second user interface element with an indication that the one or more models are valid. In some implementations, the system 100 can associate a user interface element with an indication that the newly generated model is being used in production. In some implementations, the system 100 can associate a user interface element with a prompt, requesting that the user approve the newly generated model before the system 100 integrates the newly generated model into the system 100.

At block 712, the system 100 automatically updates the GUI to display the second user interface element. After the system 100 updates the GUI, the routine 700 may proceed to block 608 of FIG. 6 where the system 100 utilizes the newly generated model in production, where the newly generated model is used to associate one or more user interface elements with one or more logging actions and/or classifications based on the newly determined probabilities.

Example Implementation of an Optimized Habit Modeling User Interface

FIGS. 8A-8F depict an example implementation of an optimized habit modeling user interface according to various embodiments. One or more methods can be used to optimize a user interface to reduce the number of presses a user may make to select a logging action. The goal of an optimized habit modeling user interface can be stated mathematically as: Let $A=(a_1, a_2, \ldots a_n)$ be a sequence of "n" logging actions. Let the probability $(a_i)$ be the probability that the user will select an action $(a_i)$. The probabilities will sum to one as all possible actions are considered for the relogging system such as system 100. In some examples, the goal can be to minimize the sum of the probability of each action times the number of presses needed to reach the action in the user interface. This can be shown as:

$$\sum_{i=0}^{n} \text{probability } (a_i) \times \text{presses } (a_i)$$

where $n$ is the number of buttons in the *GUI*.

FIG. 8A illustrates an example table 800A. The table can include logging actions 802A and a weekly frequency 804A for each logging action 802A that a user may log as part of a health system 100. The example table 800A of logging actions illustrated herein can be, for example, a subset of a larger list of logging actions. As stated above, the goal can be to minimize the sum of the probabilities of each action. In the example FIG. 8A, the sum of the probabilities 806A can be calculated by the system 100. In the present example, the sum of probabilities 806A is determined to be 10.85.

Figure 8B:
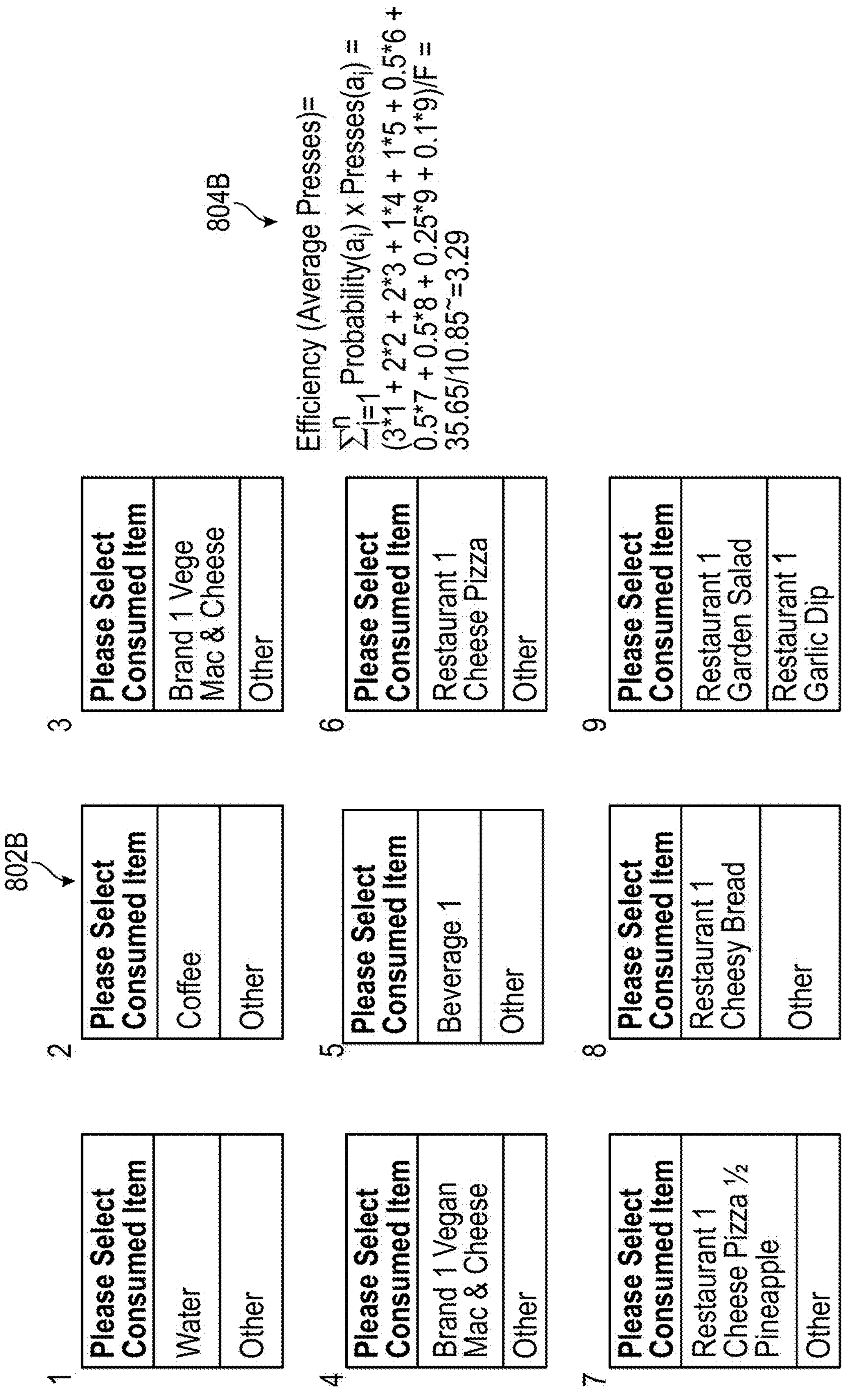

FIG. 8B illustrates example user interface elements 802B associated with logging actions and classifications sorted by the determined probability for each logging action from example table 800A. Additionally, FIG. 8B illustrates a calculated efficiency average 804B for the example table 800A. The first user interface element of the user interface elements 802B depicts the most probable logging action, namely water. Additionally, the first user interface element depicts a classification "other", which can be based on an ontology for example. If the classification "other" is selected, the system 100 can update the GUI to display the second user interface element. The second user interface element displays the second most probable logging action, namely "coffee" and the classification "other". The number of presses on the GUI required to select an individual logging action can be determined for each logging action. For example, if the user wishes to log water, the system 100 will require one press and/or click on the GUI by the user. However, if the user wishes to log "Restaurant 1 garlic dip", the system 100 would require nine presses and/or clicks on the GUI. Following the equation described above, the calculated efficiency average 804B for the example table 800A is roughly 3.29.

Figure 8C:
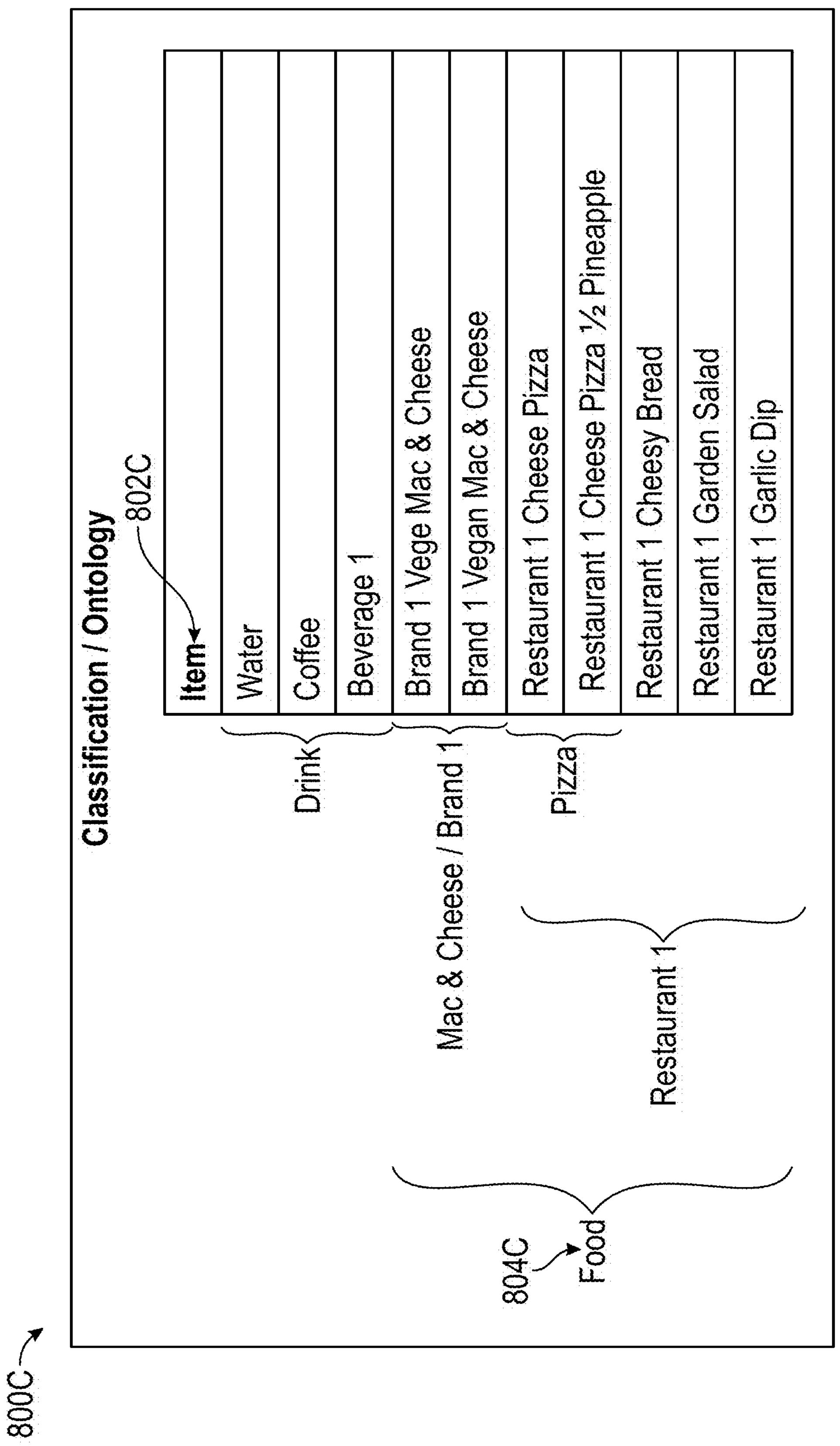

FIG. 8C depicts an example ontology 800C that can be applied to logging actions based on one or more models generated by the system 100. An example ontology 800C can be based on, for example a classification hierarchy. The ontology can alternatively be based on another hierarchy and/or another method such as a large database of hypernymy relations extracted from one or more internal and/or external sources. In the example ontology 800C, items 802C can be the same and/or similar to logging actions as depicted in in the example table 800A. The items 802C are provided as an example list of logging actions, and the system 100 may access one or more databases including more and/or less logging actions than in items 802C. Each logging action can include one or more associated classifications 804C. Classifications 804C can be any classification as described herein such as, a time of day consumed, a day of the week consumed, a location, an activity level, a hunger level, an emotion, or any other label. In the example ontology 800C, water can have the classification "drink". Further, in the example ontology 800C, the logging action "Restaurant 1 Cheese Pizza" has several associated classifications. In the present example, logging action "Restaurant 1 Cheese Pizza" has three associated classifications (e.g., "pizza", "Restaurant 1", and "Food". Applying an ontology to a list of logging actions can be used for example by a model to increase the efficiency of a GUI as described next.

Figure 8D:
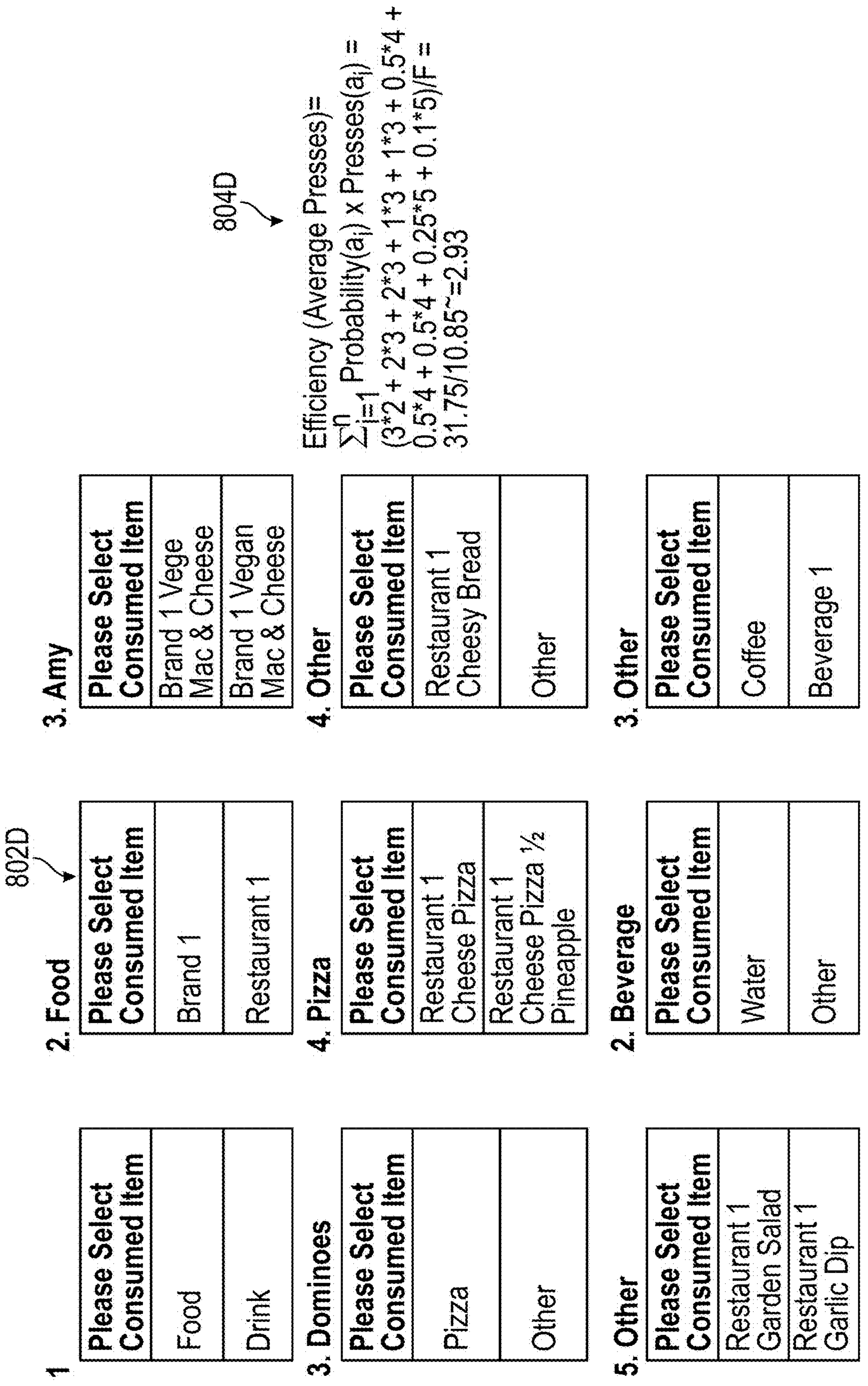

FIG. 8D illustrates example user interface elements 802D associated with logging actions and classifications. The logging actions and classifications displayed in FIG. 8D are sourced from table 800A and sorted by probability. However, unlike the example user interface elements 802B, the model used to generate user interface elements 802D applies ontology 800C having several classifications to better improve the efficiency of a GUI. For example, where user interface element 802B required nine presses on a GUI to reach the logging action "Restaurant 1 Garlic Dip" now user interface elements 802D utilizing ontology 800C, allows the user to select "Restaurant 1 Garlic Dip" in five presses by a user on a GUI. The efficiency 804D of the example user interface elements 802D with an applied ontology of 800C is calculated as well. In the present example, the calculated efficiency 804D is 2.93. In the illustrated example, the average number of presses has decreased from 3.29 to 2.93, roughly 0.36 clicks and/or presses by a user on a GUI. Consequently, efficiency (average number of presses) is improved by the addition of an ontology.

Figures 8E, 8F:
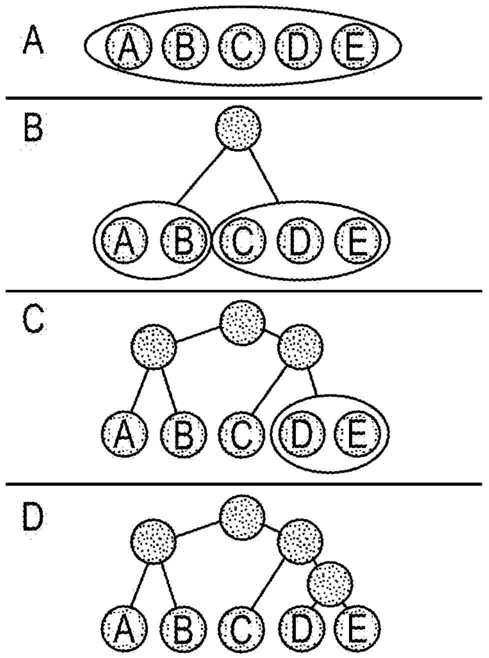

FIG. 8E-8F are examples of a table 800E and chart 800F of one or more tools that may be applied to find an efficient user interface. For example, entropy encoding schemes based on Shannon, Fano, Huffman, Elias, or the like may be employed to find efficient user interfaces. Table 800E and chart 800F illustrate examples of Fano's method. According to the Fano method, the symbols (e.g., logging actions) are arranged in order from most probable to least probable, and then divided into two sets whose total probabilities are as close as possible to being equal. All symbols then have the first digits of their codes assigned; symbols in the first set receive "0" and symbols in the second set receive "1". As long as any sets with more than one member remain, the same process is repeated on those sets, to determine successive digits of their codes. When a set has been reduced to one symbol this means the symbol's code is complete and will not form the prefix of any other symbols code.

In another implementation, an entropy encoding system can be used to determine the most efficient GUI. In information theory, entropy encoding is a lossless data compression scheme that is independent of the specific characteristics of the medium. One of the main types of entropy encoding creates and assigns a unique prefix-free code to each unique symbol that occurs in the input. The entropy encoders then compress data by reducing each fixed-length input symbol with the corresponding variable-length prefix-free output codeword. The length of each codeword is approximately proportional to the negative logarithm of the probability of occurrence of that codeword. Therefore, the most common symbols may use the shortest codes. In a further example, the Hoffman encoding system can be used to determine the most efficient GUI. The Hoffman encoding process briefly includes determining the frequencies of occurrence for each symbol in a set of source data; creating a binary tree by iteratively combining the two least frequent symbols until all symbols are include, where the frequency of each node is the sum of the frequencies of its child nodes; and finally, each symbol is assigned a binary code based on the path taken to traverse the tree.

Example Bootstrapping Process for Developing a User-Specific Ontology

Figure 9A:
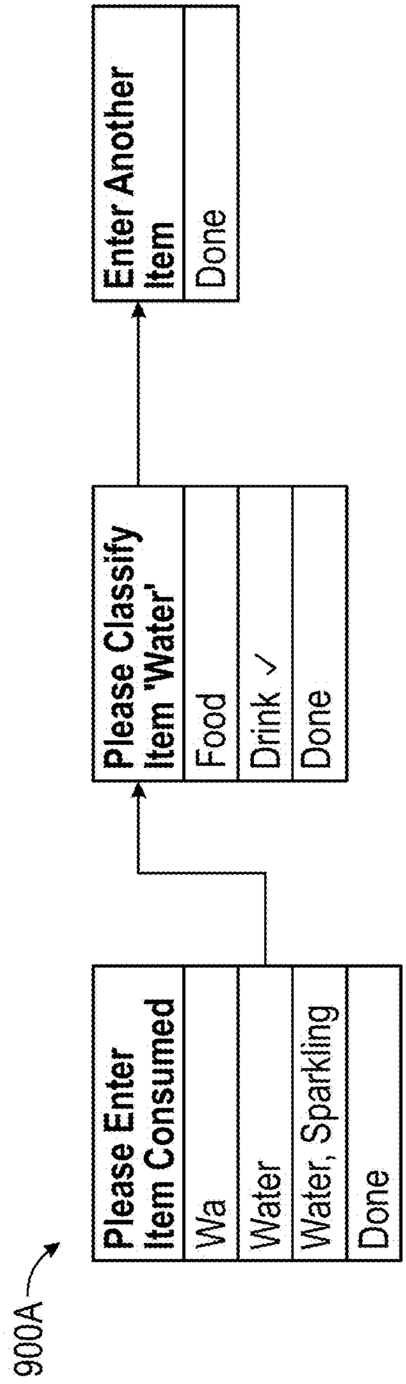
FIG. 9A-9C illustrates an example bootstrapping process for configuring a classification hierarchy.
Figure 9B:
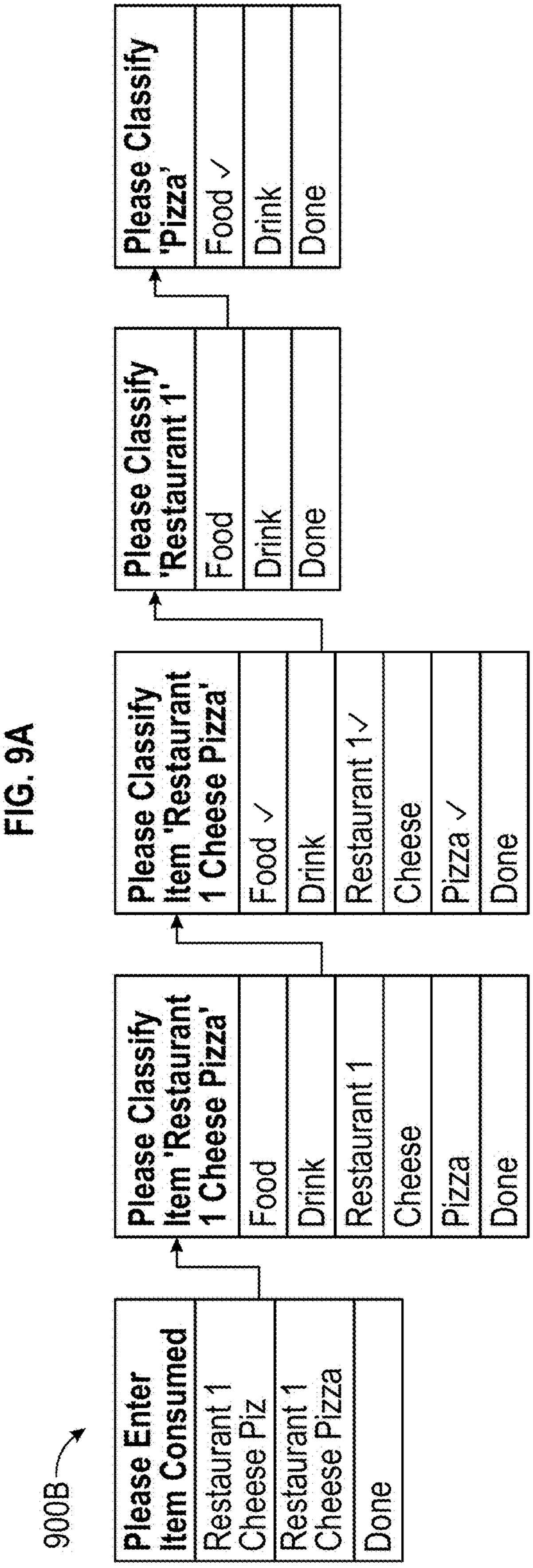
Figure 9C:
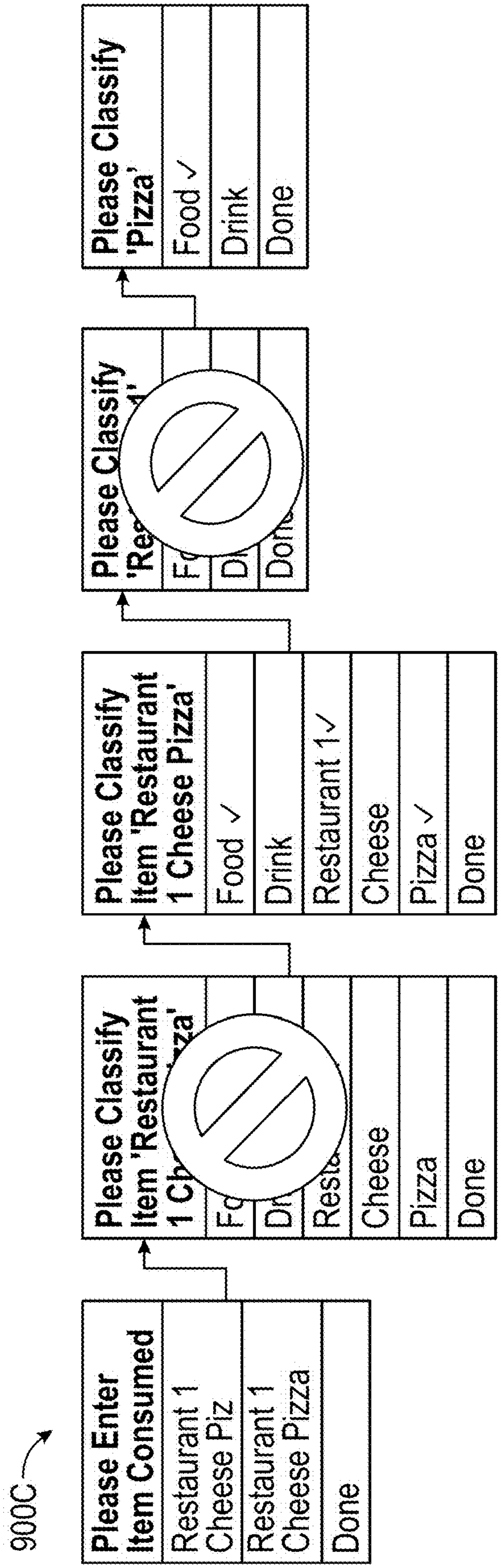

FIG. 9A-9C illustrates an example bootstrapping process. The bootstrapping process can be executed by, for example, the onboarding module 214. The bootstrapping process can be utilized to customize one or more ontologies, and/or to customize a model for a specific user. The bootstrapping process can begin by presenting one or more user interface elements to the user and request input from a user. For example, in steps 900A, the system 100 request that a user confirms one or more classifications for a logging action. In the example steps 900A, the system 100 requests that the user first enter a logging action. The user has typed in "wa" and the system 100 has updated the GUI with one or more additional user interface elements "water" "water, sparking" and "done". After the user selects water, the system 100 may request that the user confirm a classification for the water. In the example steps 900A, the user has selected "drink" as the classification for water. Once the user selects the classification drink, the system presents a prompt that the example steps 900A are completed. The system 100 may now update on ontology based on the user's input to further improve the efficiency of the GUI.

FIG. 9B includes one or more example steps 900B for a bootstrapping process. In the example steps 900B, a user has input a logging action "Restaurant 1 Cheese Piz" and the system 100 has determined that the user is requesting to log the action "Restaurant 1 Cheese Pizza". Next, the system 100 updates one or more user interface elements with a list of possible classifications for "Restaurant 1 Cheese Pizza".

The user may select one or more classifications associated with the logging action "Restaurant 1 Cheese Pizza" which can be used to update a classification hierarchy. Next, the user selects three classifications, namely "food", "Restaurant 1", and "Pizza". Further, the system 100 may receive the user selections and, based on those selections, request additional input to further classify one or more of the selected classifications. In the present example steps, 900B the system 100 has presented an updated a user interface element, requesting that the user select a further classification for "Restaurant 1" and for "Pizza".

FIG. 9C illustrates an optimized list of steps 900C as part of the bootstrapping process described in steps 900A and 900B. In the example optimized bootstrapping process illustrated in steps 900C, once the user selects logging action "Restaurant 1 Cheese Piz" the system 100 can automatically update a user interface element to display previously logged classifications for "Restaurant 1 Cheese Pizza". Hence, the user is not required to initially select classifications for "Restaurant 1 Cheese Pizza." Further the user may confirm the system-suggested classification are correct. The system-suggested classifications can be generated by, for example, an LLM and/or another model. Based on the confirmed classifications, the system 100 can further update a user interface element to display a confirmation that "Pizza" is classified as a "food" based on previous selections for Restaurant 1 Cheese Pizza."

Example Habit Modeling Framework Diagram

FIGS. 10A-10J depict example implementations of a habit modeling framework. The habit modeling framework can function as part of and/or in association with, for example, the event logging module 216, achievement module 218, nudges module 220, programs module 222, prediction module 224 and/or any of the other modules described herein. The habit modeling framework of FIGS. 10A-10J can collect data, apply one or more models in a model train, and/or track and predict one or habits of a user to build for example, a robust ontology, a predefined set of onboarding classifications, a list of logging actions, or the like.

A habit modeling framework can additionally be used to determine one or more patterns of a user and/or a group of users. The health patterns can be any type of pattern. For example, that a user and/or group of users eat a meal around 9:00 AM, that the user's and/or group of users are happy when they eat, and that generally the meal eaten at 9:00 AM is healthy. Determining one or more patterns can be utilized by the system 100 to determine whether to present various logging actions and classifications to optimize the GUI. One or more health patterns can be utilized by for example, the prediction module 224 to improve one or more predictions about an individual user and/or a group of users. For example, the habit modeling framework may determine a pattern that users entering logging actions at a specific location often log an unhealthy meal. The habit modeling framework may then determine that one or more restaurants and/or facilities in the area of the logging action serves unhealthy food, and provide a nudge to one or more users to warn the user that one or more locations may have unhealthy food. Likewise, the habit modeling framework may determine that a specific location generally has healthy food. The system may generate a nudge to the user, indicating that an area close to the user contains several healthy food options.

Figure 10A:
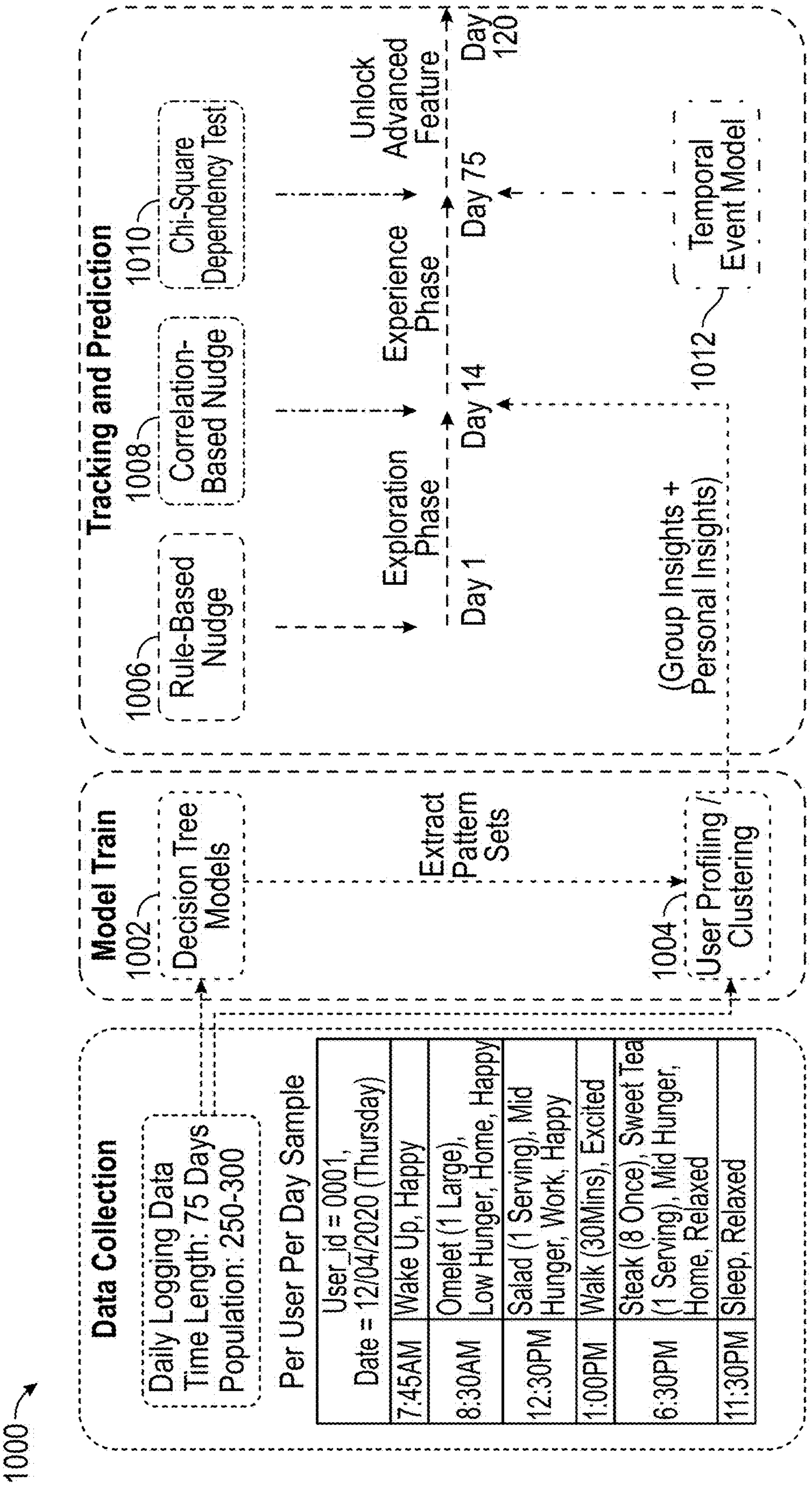

FIG. 10A depicts an example habit modeling framework 1000 according to one implementation. The habit modeling framework 1000 can include data collection, a model train, and tracking and prediction portions. The habit modeling framework 1000 begins with data collection. Data collection can include data collected from one or more users. In the example habit modeling framework 1000 data is collected for about 250 to 300 users. Additionally, the example habit modeling framework 1000 length of time for the data collection is 75 days, however this length of time can be more or less. Data collected can include an individual user's ID, a date, and a per user per day sample schedule. Additionally, other data may be collected such as any of the data described herein. The data collected can be transmitted to, for example, a model train. The model train can include decision tree model(s) 1002 and/or user profiling/clustering module 1004. At the decision tree model(s) 1002, one or more pattern sets can be extracted and transmitted to the user profiling/clustering module 1004. The results of the user profiling/clustering module 1004 can be, for example, group insights and/or personal insights into the health and/or patterns of an individual and/or a population of users. The results of the model train can be transferred to a tracking and prediction module. The tracking and prediction module can include one or more modules to provide action (e.g., motivation, alerts, and/or notifications) to an individual user and/or a group of users. For example, the tracking and prediction module can include a rule-based nudge 1006, a correlation-based nudge 1008, a chi-square dependency test 1010, and/or a temporal event model 1012. Further, the type of action generated by the habit modeling framework 1000 can be determined based on a quantity of days after data collection. In one example implementation, an exploration phase can include 1-14 days after data collection, while an experience phase can include 14 to 75 days after data collection, and advanced features can be unlocked after 75 days.

FIGS. 10B-10J illustrate models used as part of a habit modeling framework 1000. In some implementation, decision tree models, user profiling/clustering models, rule based nudges, correlation-based nudges, chi-square dependency tests, and temporal event models are used to determine one or more patterns of a user, and nudge the user to maintain, for example, a health regimen. In some implementations, a rule based nudge may or may not require a model. In some implementations, the rule-based nudge can be given by monitoring pre-defined variables. The nudge can be triggered by user logs, which may be completely user specific. The nudge type may be post-fact insight (e.g., immediate nudge after receiving a user's log). For example, a user may receive a nudge incorporating a traffic light system and text such as, "Your lunch has pepperoni pizza that is high in sodium." Additionally, the nudge can include a comparison of the user's log to one or more databases, such as a NutriScore database. For example, a nudge can include text such as, "Your 30-minute walk just reduced your NutriScore by 10." For a Rule-based nudge, training data may or may not be necessary as the code developed for a Rule-based nudge can rely on sample data.

FIG. 10B includes decision tree data 1002A. The data 1002A includes table variables, conditions, rule sets, and habit/patterns. The decision tree data 1002A can be used for habit extraction, to identify the dominant patterns that lead to bad habits, and/or patterns that can be used for clustering. In one example implementation, the data 1102A can be used to predict and/or label a next meal by a user based on one or more previous actions of the user. In the present decision tree data 1002A example, an extracted pattern can, or example, be determining whether a meal is healthy and/or unhealthy (e.g., the mean is healthy if it is less than 500 calories, and the meal is unhealthy if it is 500 calories or more). The pattern can be determined based on data 1002A such as a meal's time of day, the day of week, the meal location, whether a previous meal was healthy/unhealthy, what the previous emotion of the user was at the time of the last meal, and an activity level of the user.

Figure 10C:
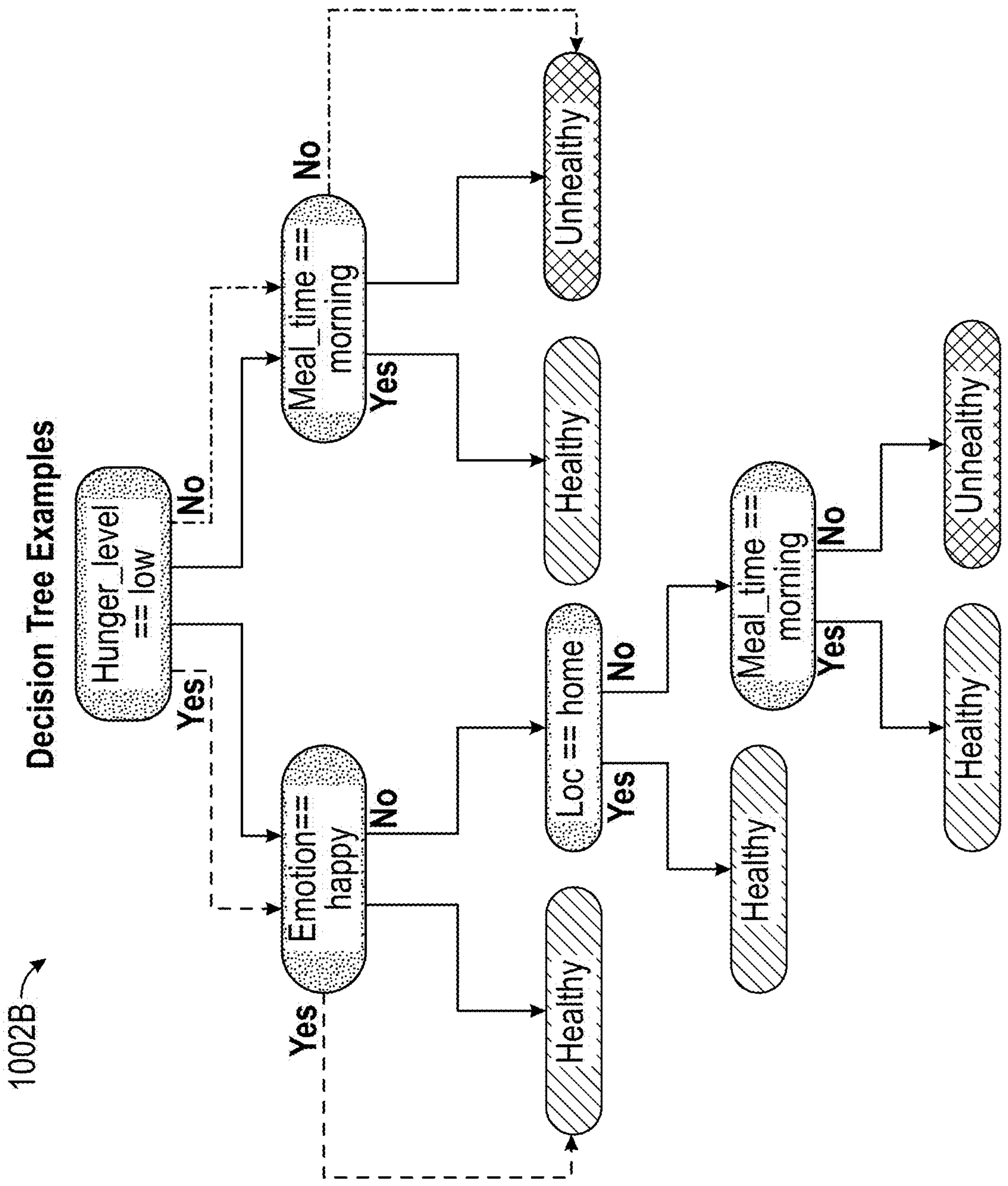

FIG. 10C is an example of a simplified decision tree 1002B based on data 1002A. The example decision tree 1002B is used to determine whether the user's patterns are healthy or unhealthy. Several patterns can be extracted from the decision tree model(s) 1002. In the present decision tree 1002B, six example patterns are displayed, however, more or less patterns can be displayed depending on the complexity of the decision tree and the patterns extracted from the decision tree. For example, a first pattern can be that when the user's hunger is not low, and the meal is not the morning, then the user is unhealthy, whereas a second pattern can be when the user's hunger is low, emotion is not happy, location is not home, and a meal's time is in the morning, then the user's meal is healthy.

Figure 10E:
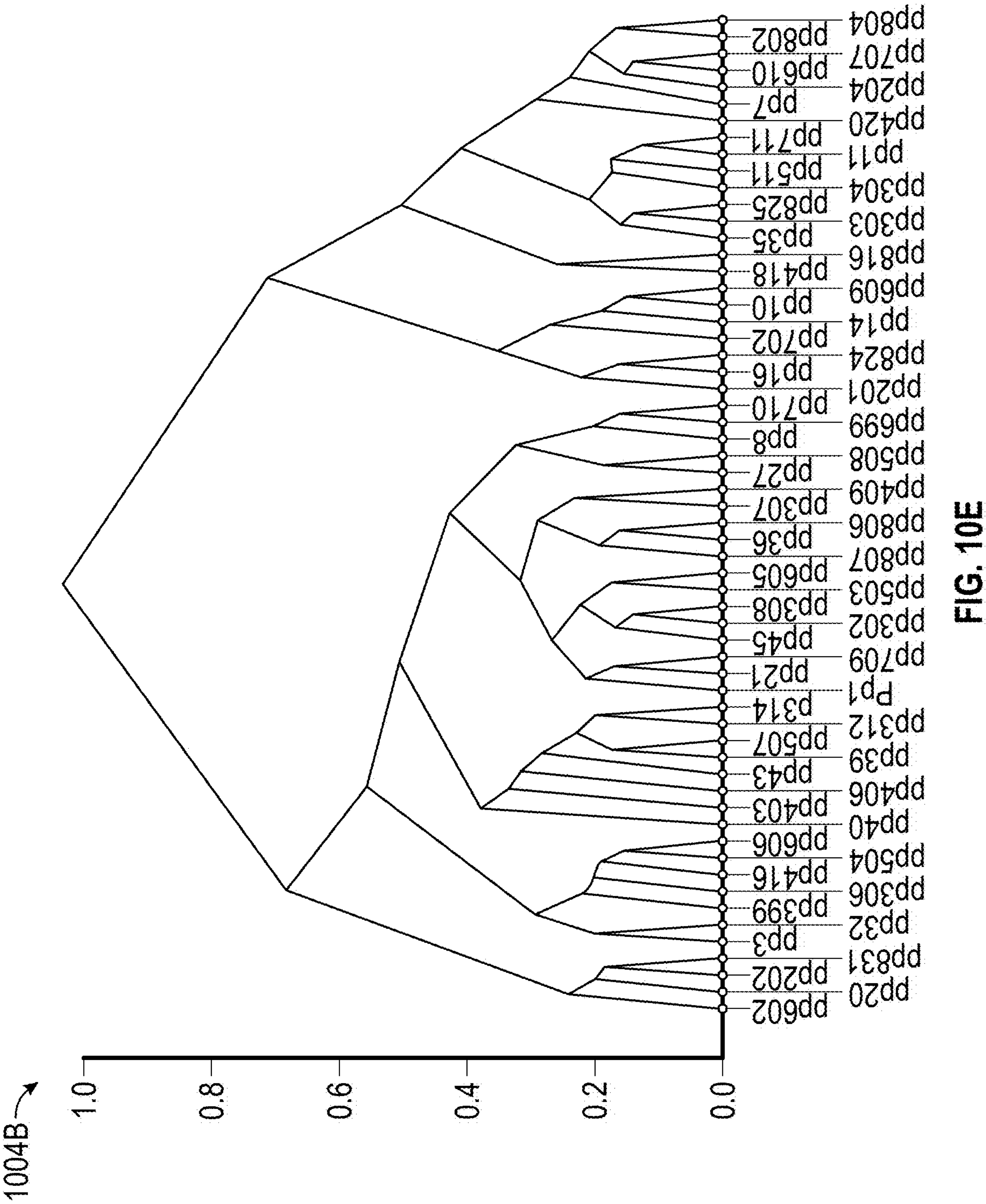
Figure 10E:
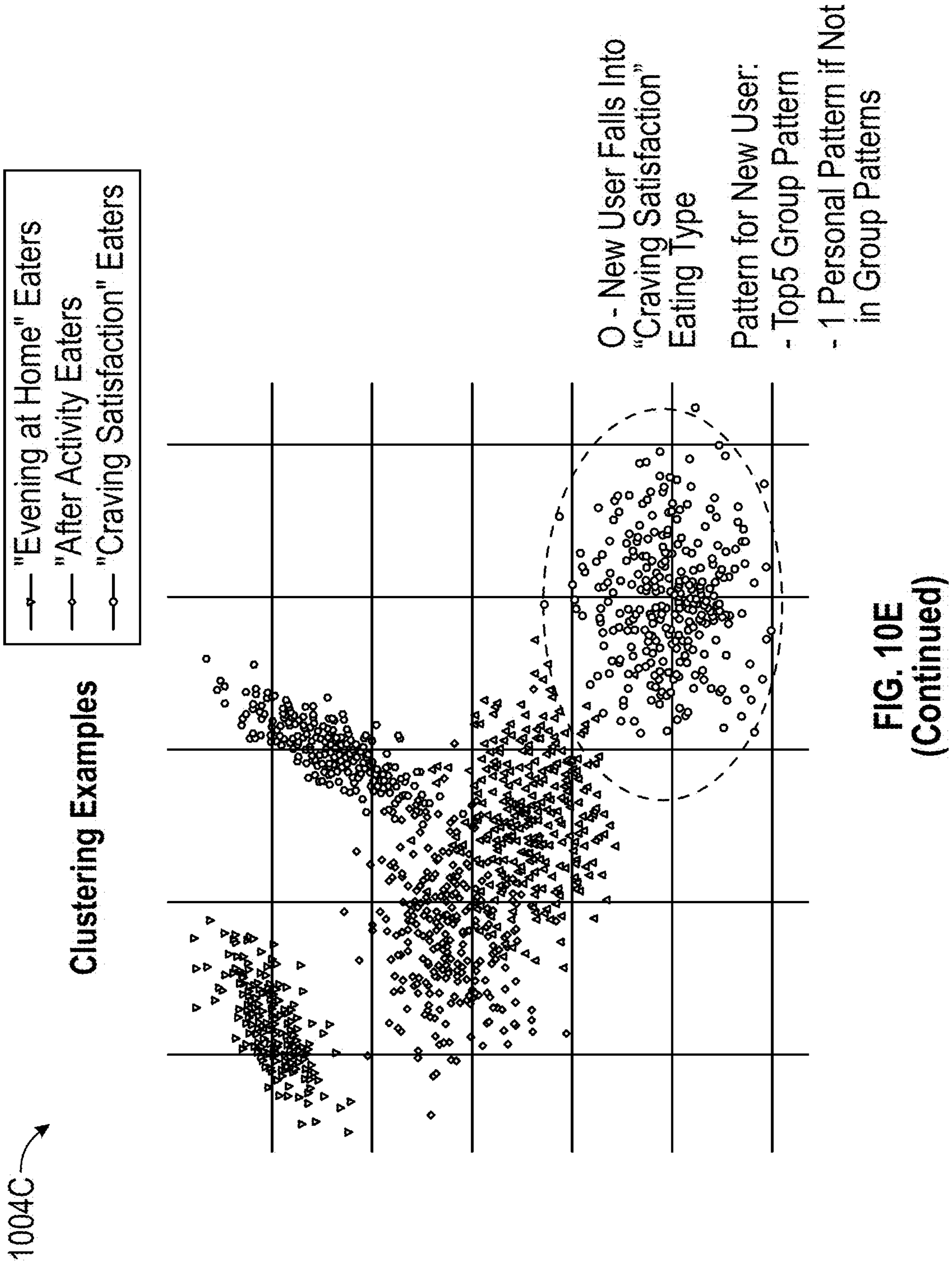

FIG. 10D-10E illustrate an example of a profiling/clustering data 1004A, an example grouping 1004B, and a cluster of participants 1004C. Profiling/clustering data 1004A can be used to develop a user-pattern matrix as recommended by, for example, the system 100. Patterns within the matrix can be dominant patterns of the user based on one or more decision trees, such as example decision tree 1002B. Calculations of the profiling/clustering data illustrated herein will not be briefly discussed. Cell $f_{i,j}$ is the frequency of user i on pattern j. Each user is represented by a vector of frequency of various eating habits. The example cluster of participants 1004C can include for example, evening at home caters, after activity caters, and craving satisfaction caters. The clustering can be ultimately used by the system 100 to send a nudge as described herein. In the example cluster of participants 1004C, an individual user can fall into the "craving satisfaction" eating type. Based on the user's eating type, for example, five of the top group habits and one of the user's personal habits can be sent as a nudge to encourage healthy eating habits.

FIG. 10F illustrates an example of a correlation-based nudge 1008A. A correlation-based nudge can be a model based on a correlation between a trigger event and a habit. The model can be personalized to an individual user. The nudge type used during a correlation based-nudge can be post-fact insight, a weekly summary, or the like. In one example, for a user that has over-slept in the last two weeks, a nudge can include text such as, "We noticed that in the past two weeks, your over-sleeping is highly correlated with excessive calorie intake during the day." A correlation-based nudge 1008A can include data such as population, duration, variables (e.g., food, activity, sleep, or the like), and whether there is any missing data. If there is no correlation detected based on the model, then no nudge may be sent to the user.

FIG. 10G is an example model of a dependency analysis 1010A. The dependency analysis 1010A can include a Chi-square analysis, having a null hypothesis that two categorical variables are independent. A test for the two variables is depicted as part of the dependency analysis 1010A. This test may be personalized and tested on a per-user basis. If the model determines to send a nudge to the user, based on the dependency analysis, the nudge type can be post-fact insight, a weekly summary, or the like. In one example, a nudge can include text such as, "Your data shows that excessive calorie intake during the day may cause over-sleep for you." For a dependency analysis 1010A, input data can include population data such as target user data, durational data such as for example, a power greater than 0.8 (chi-square value and a degrees of freedom (DOF)), one or more variables (e.g., food, activity, sleep, and/or the like), and whether there is missing data.

FIGS. 10H-10J illustrate a temporal event model. The temporal event model data 1012A can include target user data, for an example duration of 75 days. Variable can include food, activity, sleep, or the like, and there can be a missing data tolerance. In one implementation the missing data tolerance can be 5%-10%. The temporal event model 1212B illustrates that user data can be used to predict one or more future habits. An example nudge based on a temporal model 1012B can include the following, "Our algorithm predicts you will have lunch today around 1:00 PM. Don't forget to log it." A temporal model may be modified to generate an advanced model 1012C. The advanced model 1012C may be modified for long-term dependencies. The advanced model 1012C can include several dependency components, such as event intensity, personalization, propensity, short-term dependency, and long-term dependency as illustrated. The data table depicted as part of the advanced model 1012C illustrates that one or more datasets can be used in the advanced model 1012C. The data table illustrates that several events can be included across a larger population of about 4,000 and 15,000 users. Additionally, the duration for the data set can be larger in comparison to other models described herein, ranging from 7 months to 10 months. The number of samples for these datasets can be large as well, 2.1 million and 9.8 million respectively.

ADDITIONAL EXAMPLE IMPLEMENTATIONS AND DETAILS

In an implementation the system (e.g., one or more aspects of the system 100, one or more aspects of the example software environment 200, one or more aspects of the data management environment 500, and/or the like) may comprise, or be implemented in, a "virtual computing environment". As used herein, the term "virtual computing environment" should be construed broadly to include, for example, computer-readable program instructions executed by one or more processors (e.g., as described in the example of FIG. 11) to implement one or more aspects of the modules and/or functionality described herein. Further, in this implementation, one or more services/modules/engines and/or the like of the system may be understood as comprising one or more rules engines of the virtual computing environment that, in response to inputs received by the virtual computing environment, execute rules and/or other program instructions to modify operation of the virtual computing environment. For example, a request received from a user computing device may be understood as modifying operation of the virtual computing environment to cause the request access to a resource from the system. Such functionality may comprise a modification of the operation of the virtual computing environment in response to inputs and according to various rules. Other functionality implemented by the virtual computing environment (as described throughout this disclosure) may further comprise modifications of the operation of the virtual computing environment, for example, the operation of the virtual computing environment may change depending on the information gathered by the system. Initial operation of the virtual computing environment may be understood as an establishment of the virtual computing environment. In some implementations the virtual computing environment may comprise one or more virtual machines, containers, and/or other types of emulations of computing systems or environments. In some implementations the virtual computing environment may comprise a hosted computing environment that includes a collection of physical computing resources that may be remotely accessible and may be rapidly provisioned as needed (commonly referred to as "cloud" computing environment).

Implementing one or more aspects of the system as a virtual computing environment may advantageously enable executing different aspects or modules of the system on different computing devices or processors, which may increase the scalability of the system. Implementing one or more aspects of the system as a virtual computing environment may further advantageously enable sandboxing various aspects, data, or services/modules of the system from one another, which may increase security of the system by preventing, e.g., malicious intrusion into the system from spreading. Implementing one or more aspects of the system as a virtual computing environment may further advantageously enable parallel execution of various aspects or modules of the system, which may increase the scalability of the system. Implementing one or more aspects of the system as a virtual computing environment may further advantageously enable rapid provisioning (or de-provisioning) of computing resources to the system, which may increase scalability of the system by, e.g., expanding computing resources available to the system or duplicating operation of the system on multiple computing resources. For example, the system may be used by thousands, hundreds of thousands, or even millions of users simultaneously, and many megabytes, gigabytes, or terabytes (or more) of data may be transferred or processed by the system, and scalability of the system may enable such operation in an efficient and/or uninterrupted manner.

Various implementations of the present disclosure may be a system, a method, and/or a computer program product at any possible technical detail level of integration. The computer program product may include a computer-readable storage medium (or mediums) having computer-readable program instructions thereon for causing a processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer-readable storage medium (or mediums). Computer-readable storage mediums may also be referred to herein as computer-readable storage or computer-readable storage devices.

The computer-readable storage medium can be a tangible device that can retain and store data and/or instructions for use by an instruction execution device. The computer-readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Computer-readable program instructions may be callable from other instructions or from itself, and/or may be invoked in response to detected events or interrupts. Computer-readable program instructions configured for execution on computing devices may be provided on a computer-readable storage medium, and/or as a digital download (and may be originally stored in a compressed or installable format that requires installation, decompression, or decryption prior to execution) that may then be stored on a computer-readable storage medium. Such computer-readable program instructions may be stored, partially or fully, on a memory device (e.g., a computer-readable storage medium) of the executing computing device, for execution by the computing device. The computer-readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some implementations, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to implementations of the disclosure. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart(s) and/or block diagram(s) block or blocks.

The computer-readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid-state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid-state drive) either before or after execution by the computer processor.

The flowcharts and block diagrams in the Figures illustrate the architecture, functionality, and operation of possible implementations of systems, methods, and computer program products according to various implementations of the present disclosure. In this regard, each block in the flowchart or block diagrams may represent a service, module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted or optional in some implementations. The methods and processes described herein are also not limited to any particular sequence, and the blocks or states relating thereto can be performed in other sequences that are appropriate.

It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, and/or the like with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above implementations may generally (but not necessarily) be controlled and/or coordinated by operating system software, such as Mac OS, IOS, Android, Chrome OS, Windows OS (e.g., Windows XP, Windows Vista, Windows 7, Windows 8, Windows 10, Windows 11, Windows Server, and/or the like), Windows CE, Unix, Linux, SunOS, Solaris, Blackberry OS, Vx Works, or other suitable operating systems. In other implementations, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

Figure 11:
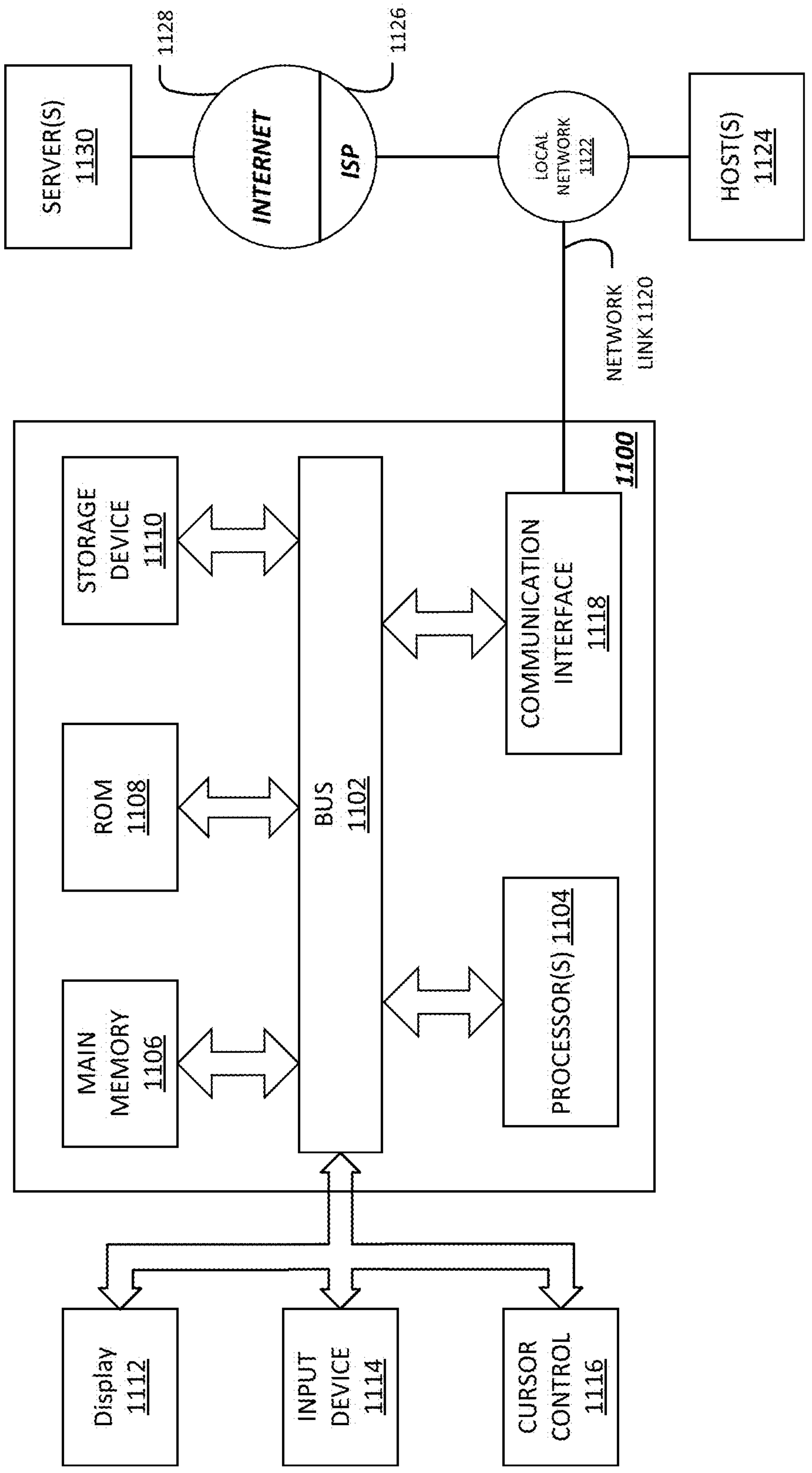
FIG. 11 is a block diagram of an example computer system consistent with various implementations of the present disclosure.

For example, FIG. 11 shows a block diagram that illustrates a computer system 1100 upon which various implementations and/or aspects (e.g., one or more aspects of the system 100, one or more aspects of the example software environment 200, one or more aspects of the data management environment 500, and/or the like) may be implemented. Multiple such computer systems 1100 may be used in various implementations of the present disclosure. Computer system 1100 includes a bus 1102 or other communication mechanism for communicating information, and a hardware processor, or multiple processors, 1104 coupled with bus 1102 for processing information. Hardware processor(s) 1104 may be, for example, one or more general purpose microprocessors.

Computer system 1100 also includes a main memory 1106, such as a random-access memory (RAM), cache and/or other dynamic storage devices, coupled to bus 1102 for storing information and instructions to be executed by processor 1104. Main memory 1106 also may be used for storing temporary variables or other intermediate information during execution of instructions to be executed by processor 1104. Such instructions, when stored in storage media accessible to processor 1104, render computer system 1100 into a special-purpose machine that is customized to perform the operations specified in the instructions. The main memory 1106 may, for example, include instructions to implement server instances, queuing modules, memory queues, storage queues, user interfaces, and/or other aspects of functionality of the present disclosure, according to various implementations.

Computer system 1100 further includes a read only memory (ROM) 1108 or other static storage device coupled to bus 1102 for storing static information and instructions for processor 1104. A storage device 1110, such as a magnetic disk, optical disk, or USB thumb drive (Flash drive), and/or the like, is provided and coupled to bus 1102 for storing information and instructions.

Computer system 1100 may be coupled via bus 1102 to a display 1112, such as a cathode ray tube (CRT) or LCD display (or touch screen), for displaying information to a computer user. An input device 1114, including alphanumeric and other keys, is coupled to bus 1102 for communicating information and command selections to processor 1104. Another type of user input device is cursor control 1116, such as a mouse, a trackball, or cursor direction keys for communicating direction information and command selections to processor 1104 and for controlling cursor movement on display 1112. This input device typically has two degrees of freedom in two axes, a first axis (e.g., x) and a second axis (e.g., y), that allows the device to specify positions in a plane. In some implementations, the same direction information and command selections as cursor control may be implemented via receiving touches on a touch screen without a cursor.

Computing system 1100 may include a user interface module to implement a GUI that may be stored in a mass storage device as computer executable program instructions that are executed by the computing device(s). Computer system 1100 may further, as described below, implement the techniques described herein using customized hard-wired logic, one or more ASICs or FPGAs, firmware and/or program logic which in combination with the computer system causes or programs computer system 1100 to be a special-purpose machine. According to one implementation, the techniques herein are performed by computer system 1100 in response to processor(s) 1104 executing one or more sequences of one or more computer-readable program instructions contained in main memory 1106. Such instructions may be read into main memory 1106 from another storage medium, such as storage device 1110. Execution of the sequences of instructions contained in main memory 1106 causes processor(s) 1104 to perform the process steps described herein. In alternative implementations, hard-wired circuitry may be used in place of or in combination with software instructions.

Various forms of computer-readable storage media may be involved in carrying one or more sequences of one or more computer-readable program instructions to processor 1104 for execution. For example, the instructions may initially be carried on a magnetic disk or solid-state drive of a remote computer. The remote computer can load the instructions into its dynamic memory and send the instructions over a telephone line using a modem. A modem local to computer system 1100 can receive the data on the telephone line and use an infra-red transmitter to convert the data to an infra-red signal. An infra-red detector can receive the data carried in the infra-red signal and appropriate circuitry can place the data on bus 1102. Bus 1102 carries the data to main memory 1106, from which processor 1104 retrieves and executes the instructions. The instructions received by main memory 1106 may optionally be stored on storage device 1110 either before or after execution by processor 1104.

Computer system 1100 also includes a communication interface 1118 coupled to bus 1102. Communication interface 1118 provides a two-way data communication coupling to a network link 1120 that is connected to a local network 1122. For example, communication interface 1118 may be an integrated services digital network (ISDN) card, cable modem, satellite modem, or a modem to provide a data communication connection to a corresponding type of telephone line. As another example, communication interface 1118 may be a local area network (LAN) card to provide a data communication connection to a compatible LAN (or WAN component to communicated with a WAN). Wireless links may also be implemented. In any such implementation, communication interface 1118 sends and receives electrical, electromagnetic, or optical signals that carry digital data streams representing various types of information.

Network link 1120 typically provides data communication through one or more networks to other data devices. For example, network link 1120 may provide a connection through local network 1122 to a host computer 1124 or to data equipment operated by an Internet Service Provider (ISP) 1126. ISP 1126 in turn provides data communication services through the worldwide packet data communication network now commonly referred to as the "Internet" 1128. Local network 1122 and Internet 1128 both use electrical, electromagnetic, or optical signals that carry digital data streams. The signals through the various networks and the signals on network link 1120 and through communication interface 1118, which carry the digital data to and from computer system 1100, are example forms of transmission media.

Computer system 1100 can send messages and receive data, including program code, through the network(s), network link 1120 and communication interface 1118. In the Internet example, a server 1130 might transmit a requested code for an application program through Internet 1128, ISP 1126, local network 1122 and communication interface 1118.

The received code may be executed by processor 1104 as it is received, and/or stored in storage device 1110, or other non-volatile storage for later execution.

As described above, in various implementations certain functionality may be accessible by a user through a web-based viewer (such as a web browser), or other suitable software program). In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain implementations, one or more of the computing devices and/or systems of the disclosure may include mobile computing devices, and user interfaces may be accessible through such mobile computing devices (for example, smartphones and/or tablets).

Many variations and modifications may be made to the above-described implementations, the elements of which are to be understood as being among other acceptable examples. All such modifications and variations are intended to be included herein within the scope of this disclosure. The foregoing description details certain implementations. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain implementations include, while other implementations do not include, certain features, elements, and/or steps. Thus, such conditional language is not generally intended to imply that features, elements and/or steps are in any way required for one or more implementations or that one or more implementations necessarily include logic for deciding, with or without user input or prompting, whether these features, elements and/or steps are included or are to be performed in any particular implementation.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conjunctive language such as the phrase "at least one of X, Y, and Z," or "at least one of X, Y, or Z," unless specifically stated otherwise, is to be understood with the context as used in general to convey that an item, term, and/or the like may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain implementations require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general-purpose computer comprising one or more processors should not be interpreted as excluding other computer components, and may possibly include such components as memory, input/output devices, and/or network interfaces, among others.

The term "model," as used in the present disclosure, can include any computer-based models of any type and of any level of complexity, such as any type of sequential, functional, or concurrent model. Models can further include various types of computational models, such as, for example, artificial neural networks ("NN"), language models ("LMs") (e.g., large language models ("LLMs")), artificial intelligence ("AI") models, machine learning ("ML") models, and/or the like.

A Language Model ("LM") is any algorithm, rule, model, and/or other programmatic instructions that can predict the probability of a sequence of words. A language model may, given a starting text string (e.g., one or more words), predict the next word in the sequence. A language model may calculate the probability of different word combinations based on the patterns learned during training (based on a set of text data from books, articles, websites, audio files, and/or the like). A language model may generate many combinations of one or more next words (and/or sentences) that are coherent and contextually relevant. Thus, a language model can be an advanced artificial intelligence algorithm that has been trained to understand, generate, and manipulate language. A language model can be useful for natural language processing, including receiving natural language prompts and providing natural language responses based on the text on which the model is trained. A language model may include an n-gram, exponential, positional, neural network, and/or other type of model.

A Large Language Model ("LLM") is any type of language model that has been trained on a larger data set and has a larger number of training parameters compared to a regular language model. An LLM can understand more intricate patterns and generate text that is more coherent and contextually relevant due to its extensive training. Thus, an LLM may perform well on a wide range of topics and tasks. An LLM may comprise a neural network trained using self-supervised learning. An LLM may be of any type, including a Question Answer ("QA") LLM that may be optimized for generating answers from a context.

A data store can be any computer-readable storage medium and/or device (or collection of data storage mediums and/or devices). Examples of data stores include, but are not limited to, optical disks (e.g., CD-ROM, DVD-ROM, and the like), magnetic disks (e.g., hard disks, floppy disks, and the like), memory circuits (e.g., solid state drives, random-access memory (RAM), and the like), and/or the like. Another example of a data store is a hosted storage environment that includes a collection of physical data storage devices that may be remotely accessible and may be rapidly provisioned as needed (commonly referred to as "cloud" storage).

A database can be any data structure (and/or combinations of multiple data structures) for storing and/or organizing data, including, but not limited to, relational databases (e.g., Oracle databases, PostgreSQL databases, MySQL databases and the like), non-relational databases (e.g., NoSQL databases, and the like), in-memory databases, spreadsheets, as comma separated values ("CSV") files, extensible markup language ("XML") files, TEXT ("TXT") files, flat files, spreadsheet files, and/or any other widely used or proprietary format for data storage. Databases are typically stored in one or more data stores. Accordingly, each database referred to herein (e.g., in the description herein and/or the figures of the present application) can be understood as being stored in one or more data stores. Additionally, although the present disclosure may show or describe data as being stored in combined or separate databases, in various embodiments such data may be combined and/or separated in any appropriate way into one or more databases, one or more tables of one or more databases, and/or the like.

A data item can be a data representation or container for information representing a specific thing in the world that have a number of definable properties. For example, a data item can represent an entity such as a physical object, a parcel of land or other real property, a market instrument, a policy or contract, or other noun. Each data item may be associated with a unique identifier that uniquely identifies the data item. The item's attributes (e.g. metadata about the object) may be represented in one or more properties. Attributes may include, for example, a geographic location associated with the item, a value associated with the item, a probability associated with the item, an event associated with the item, and so forth.

While the above detailed description has shown, described, and pointed out novel features as applied to various implementations, it may be understood that various omissions, substitutions, and changes in the form and details of the devices or processes illustrated may be made without departing from the spirit of the disclosure. As may be recognized, certain implementations of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

EXAMPLE CLAUSES

Examples of the implementations of the present disclosure can be described in view of the following example clauses. The features recited in the below example implementations can be combined with additional features disclosed herein. Furthermore, additional inventive combinations of features are disclosed herein, which are not specifically recited in the below example implementations, and which do not include the same features as the specific implementations below. For sake of brevity, the below example implementations do not identify every inventive aspect of this disclosure. The below example implementations are not intended to identify key features or essential features of any subject matter described herein. Any of the example clauses below, or any features of the example clauses, can be combined with any one or more other example clauses, or features of the example clauses or other features of the present disclosure.

Clause 1. A computing system comprising: one or more processors; and non-transitory computer-readable media storing instructions that when executed by the one or more computer processors, causes the computing system to perform operations comprising: causing presentation of a graphical user interface, the graphical user interface being associated with patient health data, wherein the graphical user interface is configured to: display one or more user interface elements, wherein each user interface element is associated with one or more logging actions and one or more classifications; receive information identifying a logging action and at least one classification associated with the logging action; generate by the processor, one or more models based on the received information, wherein at least one model comprises: a probability distribution of the one or more logging actions for a combination of the one or more classifications, wherein the probability distribution is created by assigning a probability to each of the one or more logging actions based on a weighted sum of a likelihood that a user will select at least one logging action from the one or more logging actions; based on the generated one or more models, automatically associate the one or more user interface elements with one or more logging actions based on the assigned probability of each logging action; and update the graphical user interface with at least a portion of the one or more user interface elements, wherein the updated graphical user interface displays one or more logging actions based on the likelihood that a user will select the logging action.

Clause 2. The computing system of Clause 1, wherein the one or more logging actions includes at least one of: an item of consumption or a physical activity.

Clause 3. The computing system of Clause 1, wherein the at least one classification includes at least one of a user ID, a time of day, a day of week, a location, an activity level, a hunger level, an emotion, or a label.

Clause 4. The computing system of Clause 3, wherein a time of day includes at least one of Morning (5 AM-11 AM); Midday (11 AM-5 PM); or Evening (5 PM-11 PM).

Clause 5. The computing system of Clause 3, wherein the location includes at least one of a latitude and longitude, a home, a gym, or an office.

Clause 6. The computing system of Clause 3, wherein the activity level is at least one of low-level, mid-level, or high-level.

Clause 7. The computing system of Clause 3, wherein the hunger level is at least one of low, mid, or high.

Clause 8. The computing system of Clause 3, wherein the emotion is at least one of happy, relaxed, sad, bored, stressed, angry, worried, fearful, guilty, or prideful.

Clause 9. The computing system of Clause 3, wherein the label is at least one of healthy and unhealthy, and wherein healthy is associated with at least one logging action that is less than 500 calories, and wherein unhealthy includes a logging action that is 500 calories or more.

Clause 10. The computing system of Clause 1, wherein the graphical user interface is further configured to: validate the one or more models for accuracy, by the processor, prior to automatically associating the one or more user interface elements with the one or more logging actions, and wherein validating the one or more models comprises: comparing the weighted sum of the logging actions for the one or more generated models to a threshold weighted sum.

Clause 11. The computing system of Clause 10, wherein the graphical user interface is further configured to: in response to a validated model, by the processor, adjust an efficiency improvement threshold for one or more portions of the graphical user interface.

Clause 12. The computing system of Clause 10, wherein the graphical user interface is further configured to: in response to a validated model, associate a second user interface element with an indication that the one or more models are valid; and automatically update the graphical user interface to display the second user interface element.

Clause 13. The computing system of Clause 1, wherein the one or more models include one or more constraints, and wherein the one or more constraints include at least one of a filter to exclude changes that yield marginal improvement but require substantial user interface changes, a rule defining how one or more inputs to the model can be combined, or a large language model used for predicting a next word of logging action or a classification based on a user input.

Clause 14. The computing system of Clause 1, wherein the graphical user interface is further configured to: prior to associating the one or more user interface elements with the one or more logging actions based on the assigned probability of each logging action, associate a second user interface element with a request for a user input; and automatically updating the graphical user interface to display the second user interface element.

Clause 15. The computing system of Clause 14, wherein the graphical user interface is further configured to: receive information identifying a request to associate the one or more user interface elements with the one or more logging actions based on the assigned probability of each logging action.

Clause 16. A computing system as described herein.

Clause 17. A computer-implemented method of generating an efficient graphical user interface comprising: by a system of one or more processors: displaying one or more user interface elements, wherein each user interface element is associated with one or more logging actions and one or more classifications; receiving information identifying a logging action and at least one classification associated with the logging action; generating by the processor, one or more models based on the received information, wherein at least one model comprises: a probability distribution of the one or more logging actions for a combination of the one or more classifications, wherein the probability distribution is created by assigning a probability to each of the one or more logging actions based on a weighted sum of a likelihood that a user will select at least one logging action from the one or more logging actions; based on the generated one or more models, automatically associating the one or more user interface elements with one or more logging actions based on the assigned probability of each logging action; and updating the graphical user interface with at least a portion of the one or more user interface elements, wherein the updated graphical user interface displays one or more logging actions based on the likelihood that a user will select the logging action.

Clause 18. The computer-implemented method of Clause 17, wherein the one or more logging actions includes at least one of an item of consumption or a physical activity.

Clause 19. The computer-implemented method of Clause 17, wherein the at least one classification includes at least one of a user ID, a time of day, a day of week, a location, an activity level, a hunger level, an emotion, or a label.

Clause 20. The computer-implemented method of Clause 19, wherein a time of day includes at least one of Morning (5 AM-11 AM); Midday (11 AM-5 PM); or Evening (5 PM-11 PM).

Clause 21. The computer-implemented method of Clause 19, wherein the location includes at least one of a latitude and longitude, a home, a gym, or an office.

Clause 22. The computer-implemented method of Clause 19, wherein the activity level is at least one of low-level, mid-level, or high-level.

Clause 23. The computer-implemented method of Clause 19, wherein the hunger level is at least one of low, mid, or high.

Clause 24. The computer-implemented method of Clause 19, wherein the emotion is at least one of happy, relaxed, sad, bored, stressed, angry, worried, fearful, guilty, or prideful.

Clause 25. The computer-implemented method of Clause 19, wherein the label is at least one of healthy and unhealthy, and wherein healthy is associated with at least one logging action that is less than 500 calories, and wherein unhealthy is associated with at least one logging action that is 500 calories or more.

Clause 26. The computer-implemented method of Clause 17, wherein the method further comprises: validating the one or more models for accuracy, by the processor, prior to automatically associating the one or more user interface elements with one or more logging actions, and wherein validating the one or more models comprises: comparing the weighted sum of the logging actions for the one or more generated models to a threshold weighted sum.

Clause 27. The computer-implemented method of Clause 26, wherein the method further comprises: in response to a validated model, by the processor, adjusting an efficiency improvement threshold for one or more portions of the graphical user interface.

Clause 28. The computer-implemented method of Clause 26, wherein the method further comprises: in response to a validated model, associating a second user interface element with an indication that the one or more models are valid; and automatically updating the graphical user interface to display the second interface element.

Clause 29. The computer-implemented method of Clause 17, wherein the one or more models include one or more constraints, and wherein the one or more constraints include at least one of a filter to exclude changes that yield marginal improvement but require substantial user interface changes, a rule defining how one or more inputs to the model can be combined, or a large language model used for predicting a next word of a logging action or a classification based on a user input.

Clause 30. The computer-implemented method of Clause 17, wherein the method further comprises: prior to associating the one or more user interface elements with the one or more logging actions based on the assigned probability of each logging action, associating a second user interface element with a request for a user input; and automatically updating the graphical user interface to display the second user interface element.

Clause 31. The computer-implemented method of Clause 30, wherein the method further comprises: receiving information identifying a request to associate the one or more user interface elements with the one or more logging actions based on the assigned probability of each logging action.

Clause 32. A computer-implemented method as described herein.

What is claimed is:

1. A computing system comprising:

one or more processors; and non-transitory computer-readable media storing instructions that when executed by the one or more computer processors, causes the computing system to perform operations comprising:

causing presentation of a graphical user interface, the graphical user interface being associated with patient health data, wherein the graphical user interface is configured to:

display one or more user interface elements, wherein each user interface element is associated with one or more logging actions and one or more classifications;

receive information identifying a logging action and at least one classification associated with the logging action;

generate by the processor, one or more models based on the received information, wherein at least one model comprises:

a probability distribution of the one or more logging actions for a combination of the one or more classifications, wherein the probability distribution is created by assigning a probability to each of the one or more logging actions based on a weighted sum of a likelihood that a user will select at least one logging action from the one or more logging actions;

based on the generated one or more models, automatically associate the one or more user interface elements with one or more logging actions based on the assigned probability of each logging action; and update the graphical user interface with at least a portion of the one or more user interface elements, wherein the updated graphical user interface displays one or more logging actions based on the likelihood that a user will select the logging action.

2. The computing system of claim 1, wherein the one or more logging actions includes at least one of: an item of consumption or a physical activity.

3. The computing system of claim 1, wherein the at least one classification includes at least one of a user ID, a time of day, a day of week, a location, an activity level, a hunger level, an emotion, or a label.

4. The computing system of claim 3, wherein the label is at least one of healthy and unhealthy, and wherein healthy is associated with at least one logging action that is less than 500 calories, and wherein unhealthy includes a logging action that is 500 calories or more.

5. The computing system of claim 1, wherein the graphical user interface is further configured to:

validate the one or more models for accuracy, by the processor, prior to automatically associating the one or more user interface elements with the one or more logging actions, and wherein validating the one or more models comprises:

comparing the weighted sum of the logging actions for the one or more generated models to a threshold weighted sum.

6. The computing system of claim 5, wherein the graphical user interface is further configured to: in response to a validated model, by the processor, adjust an efficiency improvement threshold for one or more portions of the graphical user interface.

7. The computing system of claim 5, wherein the graphical user interface is further configured to:

in response to a validated model, associate a second user interface element with an indication that the one or more models are valid; and automatically update the graphical user interface to display the second user interface element.

8. The computing system of claim 1, wherein the one or more models include one or more constraints, and wherein the one or more constraints include at least one of a filter to exclude changes that yield marginal improvement but require substantial user interface changes, a rule defining how one or more inputs to the model can be combined, or a large language model used for predicting a next word of logging action or a classification based on a user input.

9. The computing system of claim 1, wherein the graphical user interface is further configured to:

prior to associating the one or more user interface elements with the one or more logging actions based on the assigned probability of each logging action, associate a second user interface element with a request for a user input; and automatically updating the graphical user interface to display the second user interface element.

10. The computing system of claim 9, wherein the graphical user interface is further configured to:

receive information identifying a request to associate the one or more user interface elements with the one or more logging actions based on the assigned probability of each logging action.

11. A computer-implemented method of generating an efficient graphical user interface comprising:

by a system of one or more processors:

displaying one or more user interface elements, wherein each user interface element is associated with one or more logging actions and one or more classifications;

receiving information identifying a logging action and at least one classification associated with the logging action;

generating by the processor, one or more models based on the received information, wherein at least one model comprises:

a probability distribution of the one or more logging actions for a combination of the one or more classifications, wherein the probability distribution is created by assigning a probability to each of the one or more logging actions based on a weighted sum of a likelihood that a user will select at least one logging action from the one or more logging actions;

based on the generated one or more models, automatically associating the one or more user interface elements with one or more logging actions based on the assigned probability of each logging action; and updating the graphical user interface with at least a portion of the one or more user interface elements, wherein the updated graphical user interface displays one or more logging actions based on the likelihood that a user will select the logging action.

12. The computer-implemented method of claim 11, wherein the one or more logging actions includes at least one of an item of consumption or a physical activity.

13. The computer-implemented method of claim 11, wherein the at least one classification includes at least one of a user ID, a time of day, a day of week, a location, an activity level, a hunger level, an emotion, or a label.

14. The computer-implemented method of claim 13, wherein the label is at least one of healthy and unhealthy, and wherein healthy is associated with at least one logging action that is less than 500 calories, and wherein unhealthy is associated with at least one logging action that is 500 calories or more.

15. The computer-implemented method of claim 11, wherein the method further comprises:

validating the one or more models for accuracy, by the processor, prior to automatically associating the one or more user interface elements with one or more logging actions, and wherein validating the one or more models comprises:

comparing the weighted sum of the logging actions for the one or more generated models to a threshold weighted sum.

16. The computer-implemented method of claim 15, wherein the method further comprises: in response to a validated model, by the processor, adjusting an efficiency improvement threshold for one or more portions of the graphical user interface.

17. The computer-implemented method of claim 15, wherein the method further comprises:

in response to a validated model, associating a second user interface element with an indication that the one or more models are valid; and automatically updating the graphical user interface to display the second interface element.

18. The computer-implemented method of claim 11, wherein the one or more models include one or more constraints, and wherein the one or more constraints include at least one of a filter to exclude changes that yield marginal improvement but require substantial user interface changes, a rule defining how one or more inputs to the model can be combined, or a large language model used for predicting a next word of a logging action or a classification based on a user input.

19. The computer-implemented method of claim 11, wherein the method further comprises:

prior to associating the one or more user interface elements with the one or more logging actions based on the assigned probability of each logging action, associating a second user interface element with a request for a user input; and automatically updating the graphical user interface to display the second user interface element.

20. The computer-implemented method of claim 19, wherein the method further comprises:

receiving information identifying a request to associate the one or more user interface elements with the one or more logging actions based on the assigned probability of each logging action.

* * * * *